United States Patent
Samadani et al.

(10) Patent No.: US 11,064,881 B2
(45) Date of Patent: Jul. 20, 2021

(54) METHOD FOR PREDICTING CONVERGENCE DISORDERS CAUSED BY CONCUSSION OR OTHER NEUROPATHOLOGY

(71) Applicant: HENNEPIN HEALTHCARE SYSTEM, INC., Minneapolis, MN (US)

(72) Inventors: Uzma Samadani, Minneapolis, MN (US); Abdullah Bin Zahid, Minneapolis, MN (US)

(73) Assignee: HENNEPIN HEALTHCARE SYSTEM, INC, Minneapolis, MN (US)

( * ) Notice: Subject to any disclaimer, the term of this patent is extended or adjusted under 35 U.S.C. 154(b) by 260 days.

(21) Appl. No.: 15/350,746

(22) Filed: Nov. 14, 2016

(65) Prior Publication Data
US 2017/0172408 A1 Jun. 22, 2017

Related U.S. Application Data
(60) Provisional application No. 62/255,011, filed on Nov. 13, 2015.

(51) Int. Cl.
*A61B 3/113* (2006.01)
*A61B 3/00* (2006.01)
(Continued)

(52) U.S. Cl.
CPC ............ *A61B 3/113* (2013.01); *A61B 3/0025* (2013.01); *A61B 3/024* (2013.01); *A61B 3/08* (2013.01);
(Continued)

(58) Field of Classification Search
None
See application file for complete search history.

(56) References Cited

U.S. PATENT DOCUMENTS

| | | | | |
|---|---|---|---|---|
| 4,838,681 A | * | 6/1989 | Pavlidis | A61B 3/113 351/210 |
| 8,500,277 B1 | * | 8/2013 | Butler | A61B 3/1015 351/205 |

(Continued)

FOREIGN PATENT DOCUMENTS

WO 2013148557 A1 10/2013

OTHER PUBLICATIONS

Contreras et al., "Effect of Cognitive Load on Eye-Target Synchronization During Smooth Pursuit Eye Movement," Brain Research, 2011, pp. 55-63, vol. 1398.

(Continued)

*Primary Examiner* — Patrick Fernandes
*Assistant Examiner* — Benjamin S Melhus
(74) *Attorney, Agent, or Firm* — Wei & Sleman LLP

(57) ABSTRACT

A method for predicting abnormal eye convergence in a human or animal subject may involve tracking eye movement of at least one eye of the subject to generate eye tracking data for the subject and using the eye tracking data to predict whether the subject has abnormal eye convergence. A method for diagnosing a brain injury in a human or animal subject may involve tracking eye movement of at least one eye of the subject to generate eye tracking data for the subject, using the eye tracking data to predict whether the subject has abnormal eye convergence, and predicting whether a brain injury has occurred in the subject, based on the prediction of whether the subject has abnormal eye convergence.

16 Claims, 13 Drawing Sheets

(51) Int. Cl.
*A61B 3/024* (2006.01)
*A61B 5/00* (2006.01)
*G16H 50/30* (2018.01)
*G16H 50/20* (2018.01)
*A61B 3/08* (2006.01)

(52) U.S. Cl.
CPC .......... *A61B 5/4064* (2013.01); *A61B 5/4076* (2013.01); *G16H 50/20* (2018.01); *G16H 50/30* (2018.01); *A61B 5/7275* (2013.01)

(56) References Cited

U.S. PATENT DOCUMENTS

| | | | | |
|---|---|---|---|---|
| 8,585,589 | B1 * | 11/2013 | Cinberg | A61B 5/1104 600/300 |
| 8,808,179 | B1 * | 8/2014 | Cinberg | A61B 5/4064 600/300 |
| 8,878,749 | B1 * | 11/2014 | Wu | G01S 17/06 345/8 |
| 9,468,370 | B1 * | 10/2016 | Shearer | A61B 3/024 |
| 9,504,380 | B1 * | 11/2016 | Quaid | A61B 3/085 |
| 2004/0075814 | A1 * | 4/2004 | Alster | A61B 3/0091 351/246 |
| 2007/0121066 | A1 * | 5/2007 | Nashner | A61B 3/0091 351/210 |
| 2007/0299360 | A1 * | 12/2007 | Snyder | A61B 5/4088 600/544 |
| 2011/0228224 | A1 * | 9/2011 | Siminou | A61B 3/0058 351/206 |
| 2013/0176534 | A1 * | 7/2013 | Frankfort | A61B 3/0091 351/209 |
| 2013/0278899 | A1 * | 10/2013 | Waldorf | A61B 3/0091 351/209 |
| 2014/0218281 | A1 * | 8/2014 | Amayeh | A61B 3/14 345/156 |
| 2014/0226131 | A1 * | 8/2014 | Lopez | G06F 3/013 351/210 |
| 2015/0112224 | A1 * | 4/2015 | Super | A61B 5/168 600/558 |
| 2016/0022136 | A1 * | 1/2016 | Ettenhofer | A61B 5/7221 600/301 |
| 2016/0139665 | A1 * | 5/2016 | Lopez | G06T 7/70 345/156 |
| 2016/0213301 | A1 * | 7/2016 | Port | A61B 5/7246 |
| 2016/0270653 | A1 * | 9/2016 | Bailey | A61B 3/103 |
| 2016/0270711 | A1 * | 9/2016 | Ashmore | A61B 5/163 |
| 2016/0278716 | A1 * | 9/2016 | Samadani | A61B 5/7278 |
| 2016/0302713 | A1 * | 10/2016 | Maruta | A61B 3/145 |
| 2017/0007119 | A1 * | 1/2017 | Cornsweet | A61B 3/113 |
| 2017/0042462 | A1 * | 2/2017 | Kiderman | A61B 5/162 |
| 2017/0367633 | A1 * | 12/2017 | Samadani | A61B 3/113 |
| 2018/0184964 | A1 * | 7/2018 | Simon | A61B 5/0017 |

OTHER PUBLICATIONS

Contreras et al., "Eye-Target Synchronization in Mild Traumatic Brain-Injured Patients," J. Biol. Phys., 2008, pp. 381-392, vol. 34.

Dickmann et al., "Prevalence of Neurological Involvement and Malformative/Systemic Syndromes in A- and V-pattern Strabismus," Ophthalmic Epidemiology, 2012, pp. 302-305, vol. 19, No. 5.

Fawcett, "Disruption and Reacquisition of Binocular Vision in Childhood and in Adulthood," Current Opinion in Ophthalmology, 2005, pp. 298-302, vol. 16.

Guestrin et al., "General Theory of Remote Gaze Estimation Using the Pupil Center and Corneal Reflections," IEEE Transactions on Biomedical Engineering, Jun. 2006, pp. 1124-1133, vol. 53, No. 6.

Heitger et al., "Impaired Eye Movements in Post-Concussion Syndrome Indicate Suboptimal Brain Function Beyond the Influence of Depression, Malingering or Intellectual Ability," Brain, 2009, pp. 2850-2870, vol. 132.

Hong et al., "Reliability of a Portable Head-Mounted Eye Tracking Instrument for Schizophrenia Research," Behavior Research Methods, 2005, pp. 133-138, vol. 37, No. 1.

Maruta et al., "Visual Tracking Synchronization as a Metric for Concussion Screening," J Head Trauma Rehabilitation, 2010, pp. 293-305, vol. 25, No. 4.

Newman-Toker et al., "Quantitative Video-Oculography to Help Diagnose Stroke in Acute Vertigo and Dizziness," Stroke, Apr. 2013, pp. 1158-1161.

Schotter et al., "Binocular Coordination: REading Stereoscopic Sentences in Depth," PLoS ONE, Apr. 2012, pp. 1-12, vol. 7, Issue 4.

Schreiber et al., "Improving Calibration of 3-D Video Oculography Systems," IEEE Transactions on Biomedical Engineering, Apr. 2004, pp. 676-679, vol. 51, No. 4.

Trojano et al., "Quantitative Assessment of Visual Behavior in Disorders of Consciousness," J. Neurol, 2012, pp. 1888-1895, vol. 259.

* cited by examiner

Table 4: T-Test for age matching

Independent Samples Test

| | | Levene's Test for Equality of Variances | | t-test for Equality of Means | | | | | 95% Confidence Interval of the Difference | |
|---|---|---|---|---|---|---|---|---|---|---|
| | | F | Sig. | t | df | Sig. (2-tailed) | Mean Difference | Std. Error Difference | Lower | Upper |
| Age | Equal variances assumed | .059 | .808 | -.026 | 62 | .979 | -.0312500 | 1.1911949 | -2.4124147 | 2.3499147 |
| | Equal variances not assumed | | | -.026 | 61.988 | .979 | -.0312500 | 1.1911949 | -2.4124241 | 2.3499241 |

Figure 5

Table 7: The Variables in the model created in an age and gender matched sample: Logistic regression:

Variables in the Equation

| | B | S.E. | Wald | df | Sig. | Exp(B) | 95% C.I.for EXP(B) | |
|---|---|---|---|---|---|---|---|---|
| | | | | | | | Lower | Upper |
| Step 4$^d$ left#distLef#value | 1026.667 | 442.174 | 5.391 | 1 | .020 | . | 3.140E69 | . |
| right#distRit#value | 2241.677 | 832.901 | 7.244 | 1 | .007 | . | 3.816E264 | . |
| conj#varXtopbotRatio#value | -.369 | .179 | 4.243 | 1 | .039 | .692 | .487 | .982 |
| left#varYtop#value | -22.628 | 9.441 | 5.744 | 1 | .017 | .000 | .000 | .016 |
| Constant | -5.328 | 1.693 | 9.901 | 1 | .002 | .005 | | | a. Variable(s) entered on step 1: left#distLef#value.
b. Variable(s) entered on step 2: left#varYtop#value.
c. Variable(s) entered on step 3: right#distRit#value.
d. Variable(s) entered on step 4: conj#varXtopbotRatio#value.

Figure 6

METHOD FOR PREDICTING CONVERGENCE DISORDERS CAUSED BY CONCUSSION OR OTHER NEUROPATHOLOGY

CROSS-REFERENCE TO RELATED APPLICATION

This application claims the benefit under 35 U.S.C. § 119 U.S. Provisional Application No. 62/255,011, filed Nov. 13, 2015. The foregoing application is hereby incorporated herein by reference in its entirety for all purposes.

INCORPORATION BY REFERENCE

All patent applications, patents and other publications referenced in this application are hereby incorporated by reference in their entirety. For example, Patent Cooperation Treaty Application No. PCT/US2013/033672, filed Mar. 25, 2013, and U.S. Provisional Patent Application No. 61/881,014, filed Sep. 23, 2013, are both hereby incorporated by reference in their entireties.

FIELD OF THE INVENTION

The present invention relates to medical diagnostic methods. More specifically, the invention relates to a method for predicting, assessing and/or quantifying convergence disorders caused by concussion or other neuropathology.

BACKGROUND

Traumatic brain injury (TBI) is a very serious and significant health problem. Every year, at least 1.7 million TBIs occur in the United States, and they are a contributing factor in about one third of all injury-related deaths. The incidence of TBI, as measured by combined emergency department (ED) visits, hospitalizations, and deaths, rose steadily from 2001 to 2010. For example, from 2001 to 2010, TBI rates increased from 521 to 824 per 100,000 population. Between 3.2 and 5.3 million people (1.1%-1.7% of the U.S. population) live with long-term disabilities that result from TBI. These are likely underestimates of the prevalence of TBI, because they do not include persons with TBI sequelae who were treated and released from EDs, those who sought care in other health-care settings, and those who did not seek treatment.

Traumatic brain injuries can be very challenging to diagnose and treat. One of the primary challenges posed by TBI is the heterogeneous nature of such injury, in terms of etiology, anatomic sequelae, and physiologic and psychologic impact. The etiology of injury affects the anatomic sequelae and ranges from global mechanisms, such as acceleration/deceleration and blast, to potentially more focal mechanisms, such as blunt impact and penetrating trauma. Some injury mechanisms result in structural changes to the brain that can be visualized using conventional imaging, such as MRI and CT scan, while other injuries appear radiographically normal.

Concussion is probably the best known form of TBI and is the most common form of civilian radiographically normal brain injury. Concussion most often results from blunt impact, and it is typically not detectable by conventional radiographic imaging, such as computed tomography (CT) scan. Concussion is defined in part by transient loss or disruption of neurologic function. The term "subconcussion" is used to describe the sequelae of brain injury in the absence of transient loss or disruption of neurologic function. For the purposes of the present application, the terms "concussion," "subconcussion" and "blast injury" may sometimes be referred to generally as "non-structural brain injury."

Blast injury resembles blunt impact brain injury, in that both may be associated with radiographically apparent cerebral edema and intracranial hemorrhage. Like concussion, blast injury is very frequently radiographically normal, yet mild or moderate blast injury is strongly associated with post-traumatic stress disorder and other cognitive dysfunctions. Blunt impact and penetrating trauma can result in both diffuse and focal injury. One mechanism by which focal brain injury leads to neurologic damage is cortical spreading depression, which is currently only thought measurable using invasive means.

Brain injury may be associated with short term sequelae, including headaches and memory problems, and longer term problems, including dementia, Parkinsonism and motor-neuron disease. Both concussion and mild blast injury may be associated with post-traumatic stress disorder and cognitive impairment. Clinical tests for concussion are not very reliable, and thus concussion remains a diagnosis that is difficult to treat, because it is difficult to detect.

Many cases of trauma result in elevated intracranial pressure. If untreated, acute elevations in intracranial pressure (ICP) due to brain injury can result in permanent neurologic impairment or death.

One method of diagnosing and pinpointing TBI is eye movement tracking. The clinical basis for eye tracking as a diagnostic for brain injury has ancient roots. 3500 years ago, Greek physicians wrote a surgical treatise stating that eyes that are askew may be evidence of brain injury. Prior to the invention of radiographic imaging, the assessment of eye movements was a major modality of diagnosis of neurologic impairment, with entire textbooks dedicated to this topic. Modern era optometrists can detect abnormal eye movements in up to 90% of patients with so-called "mild" traumatic brain injury or concussion.

The most commonly detected abnormal eye movement associated with brain injury is a vergence problem. Vergence is the ability of the both eyes to focus together on a single point. If the point moves closer to the nose, the pupils converge. Following the point in space—or while watching TV—requires sustained vergence. Previous studies using eye tracking to assess patients with post-concussive symptoms suggest that these deficits may persist beyond the acute phase of injury.

Traumatic brain injury can impact eye movement through a multitude of mechanisms, including direct compression of cranial nerves, trauma to cranial nerves, injury to cranial nerve nuclei and supranuclear impacts. In eye movement tracking, an eye tracker device is used to measure movements of the eyes, and the movements are used to assess brain function. Spatial calibration of the eye tracker device is often performed for each individual being tracked. With calibration, the eye-tracker measures the relative position of pupil and corneal reflection for a period of about 400-800 ms, while the subject looks at a target or targets of known position, to generate meaningful spatial coordinates during subsequent pupil movement. One problem with spatial calibration, however, is that the process assumes relatively preserved neurologic function, because it requires the subject to follow commands and look at specific points.

It is conceivable that the process of spatial calibration may mask deficits in ocular motility. If there is a persistent and replicable weakness in movement of an eye, the camera will interpret the eye's ability to move in the direction of that weakness as the full potential range of motion in that direction, due to the calibration process. In other words, if the subject is directed to look at a position but consistently only moves halfway there, the calibration process will account for that when tracking subsequent eye movements and interpret movements to the halfway point as occurring at the full range of normal motion. If, during calibration, one eye only makes it half-way to the target, but the other eye is fully there, the camera will interpret both eyes as being together when one performs half the eye movement as the other. Thus, binocular spatial calibration may preclude detection of disconjugate gaze, unless each eye is calibrated separately using a dichoptic apparatus.

Conjugate gaze is the motion of both eyes in the same direction at the same time. Disconjugate gaze, or strabismus, is a failure of the eyes to turn together in the same direction. Normal coordinated movements of the eyes produces conjugate gaze, in which the eyes are aligned for binocular 3-dimensional vision. Misalignment results in loss of this vision. With the visual axis of each eye fixated on a different point, diplopia (or double vision) usually results and may be perceived as a blurred image if the two images are very closely aligned. However, if the image from the weaker eye is suppressed by higher cortical centers, there is only one image with loss of visual acuity (or a blurred image).

Assessment of eye movement conjugacy is commonly performed by primary care physicians, neurologists, ophthalmologists, neurosurgeons, emergency medicine doctors, and trauma surgeons, to rapidly assess global neurologic functioning. When various eye movement tests are performed, in conjunction with the remainder of the neurophthalmic and physical evaluation, one can localize neurologic lesions and quantitate ocular motility deficits with great accuracy. Despite this capability, however, these tests are not used routinely in the emergency setting, due to the need for a trained practitioner to administer them, the requirement for sophisticated equipment, and the urgent nature of many neurologic disorders.

Progress has been made in methods and kits for using eye tracking to assess brain injury. For example, U.S. Provisional Application No. 61/881,014, filed Sep. 23, 2013, the disclosure of which is herein incorporated by reference in its entirety, teaches methods for tracking eye movement, and methods and kits for assessing conjugacy and disconjugacy of gaze and strabismus. Despite this progress, however, it would be advantageous to have further improvements in methods, systems and kits for assessing brain injury using eye tracking. Ideally, such methods, systems and kits could be used not only for assessing and diagnosing concussion, but could also be used for assessing other TBI and/or other neuropathology.

BRIEF DESCRIPTION OF THE DRAWINGS

FIG. 5 is a table listing metrics in a logistic regression model that correlated eye tracking metrics to the state of being concussed.

FIG. 6 is a table of gender for the validation population.

BRIEF SUMMARY

Figure 1:
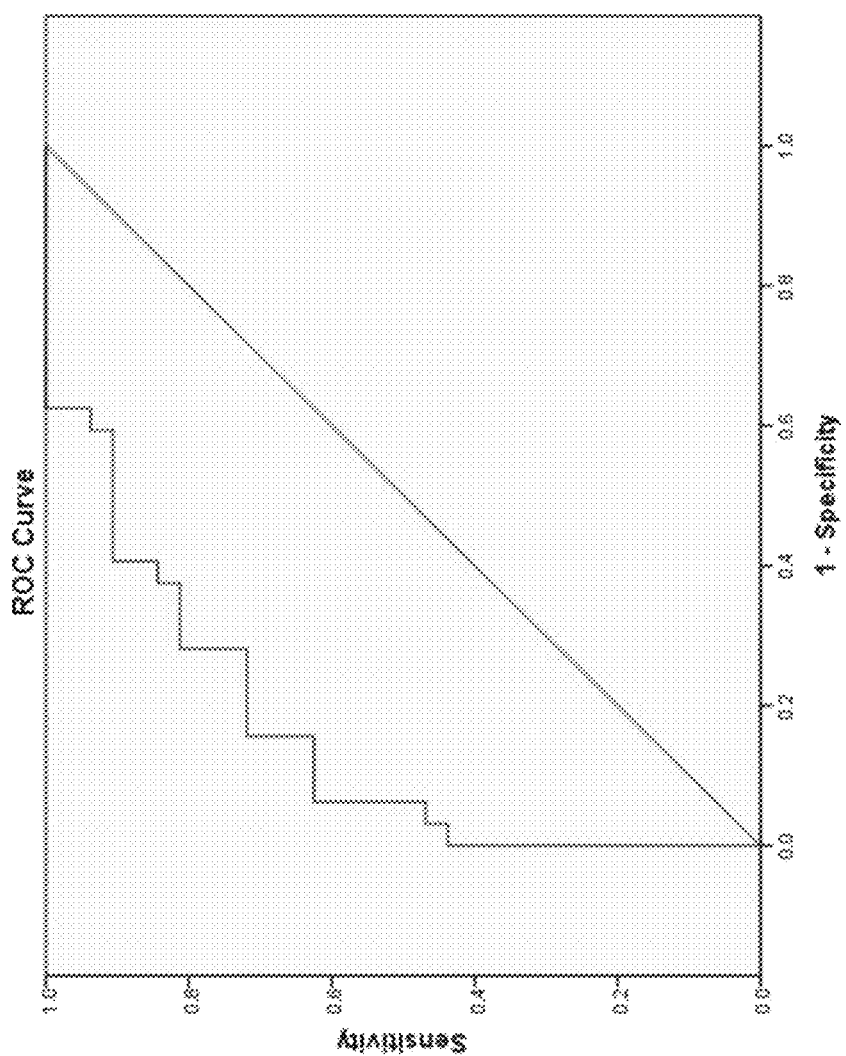
FIG. 1 is a graph showing the receiver operating curve in a balanced model for pediatric concussion.
Figure 2:
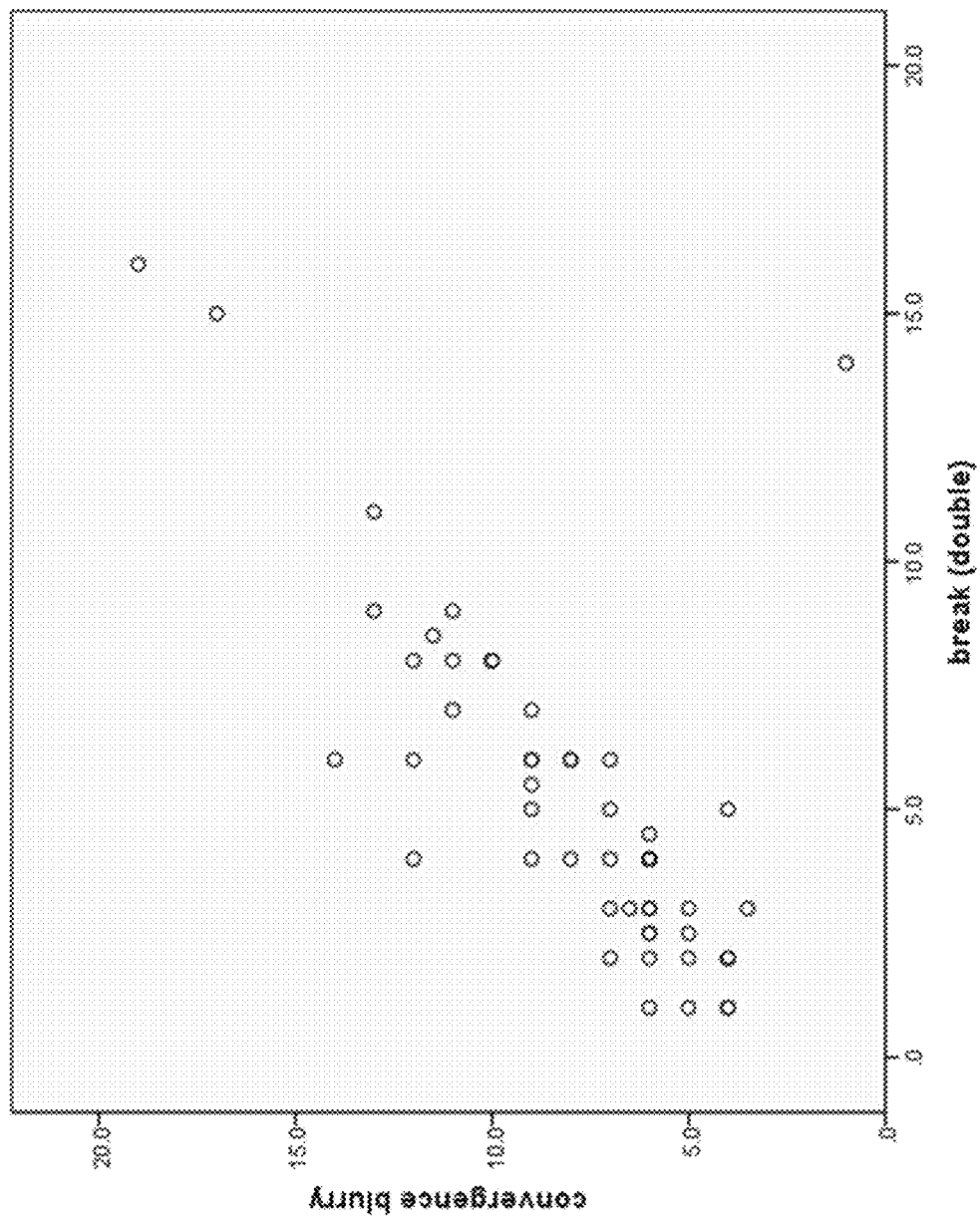
FIG. 2 is a scatterplot showing the convergence blurry and break (double) have a very smooth relationship. Spearman correlation of 0.752 (p-value<0.001)
Figure 3:
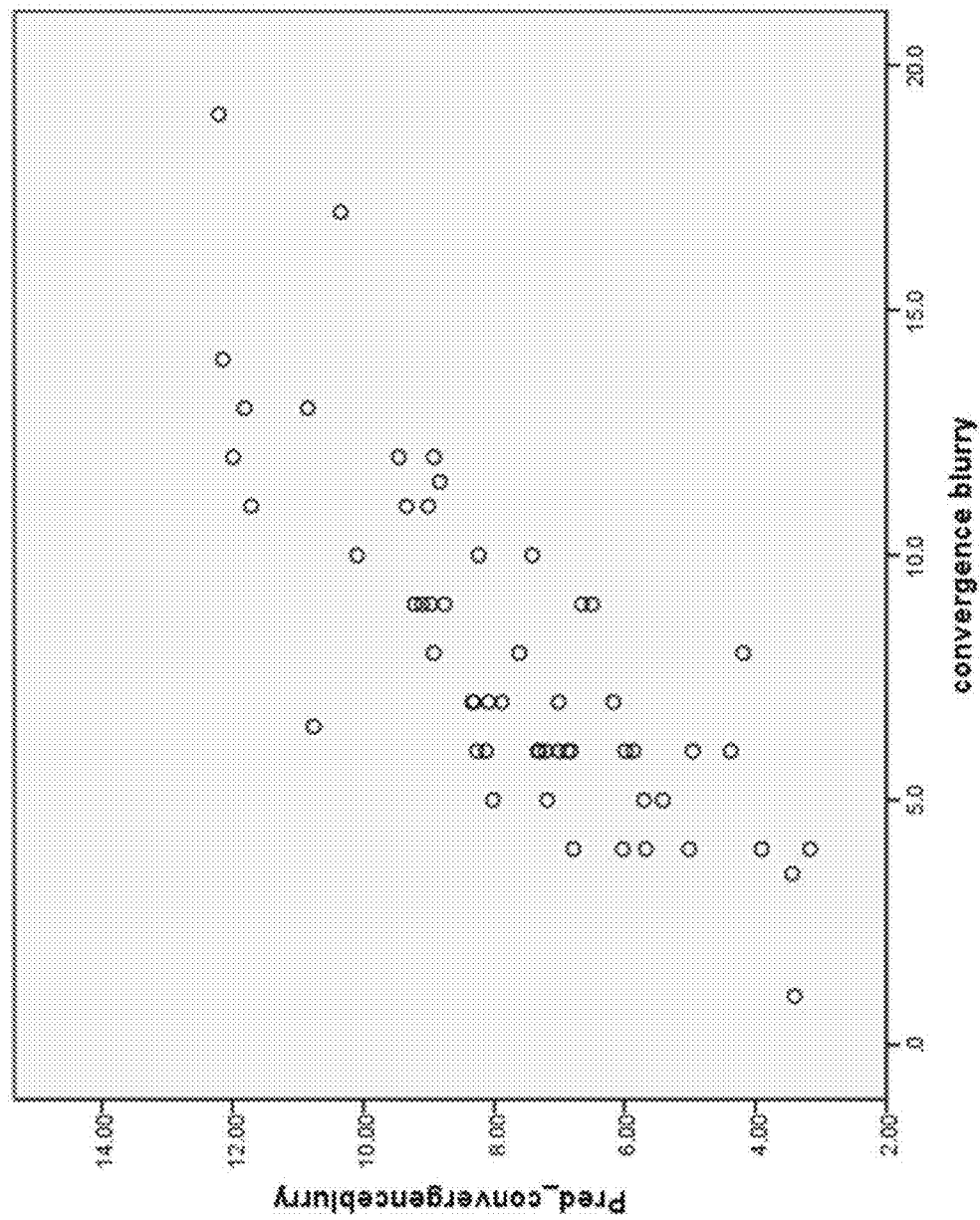
FIG. 3 is a scatterplot showing the relationship of Model predictions to actual values of convergence blurry spearman correlation of 0.785 (p-value<0.001).

In one aspect, a method for predicting abnormal eye convergence in a human or animal subject may involve tracking eye movement of at least one eye of the subject to generate eye tracking data for the subject and using the eye tracking data to predict whether the subject has abnormal eye convergence. In some embodiments, tracking eye movement may involve tracking movement of both eyes of the subject. In some embodiments, generating the eye tracking data may involve analyzing the tracked eye movement and comparing the tracked eye movement to a normal or mean eye movement. In some embodiments, generating the eye tracking data may further involve, after the comparing step, calculating a standard deviation or p value for the tracked eye movement as compared to the normal or mean eye movement. Comparing the tracked eye movement may involve comparing eye movement of one eye of the subject to eye movement of the other eye of the subject. Alternatively, comparing the tracked eye movement may involve comparing eye movement of both eyes of the subject to eye movement of one or both eyes of one or more other subjects or controls.

In some embodiments, the method may also involve predicting whether a brain injury has occurred in the subject, based on the prediction of whether the subject has abnormal eye convergence. For example, predicting whether the brain injury has occurred may involve predicting whether a concussion has occurred. In some embodiments, the eye movement is tracked for at least 40 seconds.

In another aspect, a method for diagnosing a brain injury in a human or animal subject may involve: tracking eye movement of at least one eye of the subject to generate eye tracking data for the subject; using the eye tracking data to predict whether the subject has abnormal eye convergence; and predicting whether a brain injury has occurred in the subject, based on the prediction of whether the subject has abnormal eye convergence. In some embodiments, predicting whether the brain injury has occurred involves predicting whether a concussion has occurred.

In another aspect, a method for measuring, assessing and/or quantifying abnormal eye convergence in a human or animal subject may involve tracking eye movement of at least one eye of the subject to generate eye tracking data for the subject and using the eye tracking data to measure, assess and/or quantify eye convergence of the subject.

In another aspect, a method for measuring, assessing and/or quantifying a level of brain injury in a human or animal subject may involve tracking eye movement of at least one eye of the subject to generate eye tracking data for the subject, using the eye tracking data to predict whether the subject has abnormal eye convergence, and measuring, assessing and/or quantifying the level of brain injury in the subject, based on the prediction of whether the subject has abnormal eye convergence.

In another aspect, a method for measuring, assessing and/or quantifying brain injury in a human or animal subject may involve: tracking eye movement of at least one eye of the subject; collecting raw x and y cartesian coordinates of pupil position; normalizing the raw x and y cartesian coordinates; calculating one or more individual metrics; and measuring, assessing and/or quantifying brain injury in the subject, based at least in part on the calculated metrics. In some embodiments, the brain injury is concussion.

In another aspect, a system for predicting abnormal eye convergence in a human or animal subject may include a device for tracking eye movement and a processor integrated into or coupled with the device for processing the tracked eye movement to generate eye tracking data and predicting whether the subject has abnormal eye convergence based on the eye tracking data. The device may be any suitable eye tracking device, such as any eye tracking device described in this application, any other currently available eye tracking device, a webcam device, goggles, or the like.

In another aspect, a non-transitory computer-readable medium may have instructions stored thereon for predicting abnormal eye convergence in a human or animal subject, the instructions configured to perform the following steps: receiving eye movement data pertaining to eye movement of one or both eyes of the subject; analyzing the eye movement data of one or both eyes of the subject; comparing eye movement data of one or both eyes of the subject to a normal or mean eye movement; and predicting whether the subject has abnormal eye convergence, based on the comparison of the eye movement data. In some embodiments, the instructions may be further configured to perform the step of calculating a standard deviation or p value for eye movement of one or both eyes of the subject as compared to the normal or mean eye movement, before the predicting step. Some embodiments may further include instructions stored thereon for measuring, assessing and/or quantifying brain injury in a human or animal subject, the instructions further configured to perform the following steps: tracking eye movement of at least one eye of the subject; collecting raw x and y cartesian coordinates of pupil position; normalizing the raw x and y cartesian coordinates; and calculating one or more individual metrics.

In another aspect, a method for assessing or quantitating structural and non-structural traumatic brain injury may involve: tracking eye movement of at least one eye of the subject; analyzing eye movement of at least one eye of the subject; comparing eye movement of at least one eye of the subject to a normal or mean eye movement; and, optionally, calculating a standard deviation or p value for eye movement of at least one eye of the subject as compared to the normal or mean eye movement.

In some instances, eye movement of both eyes of the subject are tracked and analyzed. In some instances, both x and y coordinates of eye position for one or both eyes of a subject are collected for at least about 100, 500, 1,000, 5,000, 10,000, 50,000, 100,000, 200,000 or more eye positions. In some instances, the eye position is effectively the pupil position. In some instances the eye movement is tracked for about 30, 60, 90, 100, 120, 150, 180, 200, 220, 240, 270, 300, 360 or more seconds.

The comparing eye movement of at least one eye of the subject to a normal or mean eye movement may feature comparing eye movement of at least one eye of the subject to the eye movement of the other eye of the subject or may feature comparing eye movement of at least one eye of the subject to the eye movement of an eye of one or more other subjects or controls. In some instances, the comparing eye movement of at least one eye of the subject to a normal or mean eye movement may feature comparing the eye movement of both eyes of the subject to the eye movement of one or both eyes of one or more other subjects or controls.

In some instances, the method may feature collecting raw x and y cartesian coordinates of pupil position, normalizing the raw x and y Cartesian coordinates, and sorting the data by eye.

The method may also feature calculating individual metrics, such as, for instance, segment mean, segment median, and segment variance. The method may also feature calculating specific metrics such as, for example, $$L.\ \text{var}Y\text{top}=\text{Var}(\bar{y}_1, \text{average}\ k=1:5,1) \quad (13)$$

$$R.\ \text{var}Y\text{top}=\text{Var}(\bar{y}_2, \text{average}\ k=1:5,1) \quad (14)$$

$$L.\ \text{var}X\text{rit}=\text{Var}(\bar{x}_1, \text{average}\ k=1:5,2) \quad (15)$$

$$R.\ \text{var}X\text{rit}=\text{Var}(\bar{x}_2, \text{average}\ k=1:5,2) \quad (16)$$

$$L.\ \text{var}Y\text{bot}=\text{Var}(\bar{y}_1, \text{average}\ k=1:5,3) \quad (17)$$

$$R.\ \text{var}Y\text{bot}=\text{Var}(\bar{y}_2, \text{average}\ k=1:5,3) \quad (18)$$

$$L.\ \text{var}X\text{lef}=\text{Var}(\bar{x}_1, \text{average}\ k=1:5,4) \quad (19)$$

$$L.\ \text{var}X\text{lef}=\text{Var}(\bar{x}_2, \text{average}\ k=1:5,4) \quad (20)$$

$$L.\ \text{var}\text{Total}=\text{Average}(\text{Var}(\bar{x}_1, \text{average}\ k=1:5)+\text{Var}(\bar{y}_1, \text{average}\ k=1:5)) \quad (21)$$

$$R.\ \text{var}\text{Total}=\text{Average}(\text{Var}(\bar{x}_2, \text{average}\ k=1:5)+\text{Var}(\bar{y}_2, \text{average}\ k=1:5)) \quad (22)$$

or segment standard deviation and segment skew such as, for instance, $$L.\ \text{SkewTop}=\text{Skew}(\bar{y}_1, \text{average}\ k=1:5,1) \quad (27)$$

$$R.\ \text{SkewTop}=\text{Skew}(\bar{y}_2, \text{average}\ k=1:5,1) \quad (28)$$

$$L.\ \text{SkewRit}=\text{Skew}(\bar{x}_1, \text{average}\ k=1:5,2) \quad (29)$$

$$R.\ \text{SkewRit}=\text{Skew}(\bar{x}_2, \text{average}\ k=1:5,2) \quad (30)$$

$$L.\ \text{SkewBot}=\text{Skew}(y_1, \text{average}\ k=1:5,3) \quad (31)$$

$$R.\ \text{SkewBot}=\text{Skew}(y_2, \text{average}\ k=1:5,3) \quad (32)$$

$$L.\ \text{SkewLef}=\text{Skew}(\bar{x}_1, \text{average}\ k=1:5,4) \quad (33)$$

$$R.\ \text{SkewLef}=\text{Skew}(\bar{x}_2, \text{average}\ k=1:5,4) \quad (34)$$

or segment normalized skew, such as, for instance, $$SkewNorm(\bar{x}_{j,k\cdot 1}) = \frac{Skew(\bar{x}_{j,k\cdot 1})}{\sigma_{\bar{x}_{j,k\cdot 1}}}, \quad (35)$$

$$SkewNorm(\bar{y}_{j,k\cdot 1}) = \frac{Skew(\bar{y}_{j,k\cdot 1})}{\sigma_{\bar{y}_{j,k\cdot 1}}}, \quad (36)$$

L. SkewTopNorm=SkewNorm($\bar{y}_1$,average k=1:5,1)  (37)

R. SkewTopNorm=SkewNorm($\bar{y}_2$,average k=1:5,1)  (38)

L. SkewRitNorm=SkewNorm($\bar{x}_1$,average k=1:5,2)  (39)

R. SkewRitNorm=SkewNorm($\bar{x}_2$,average k=1:5,2)  (40)

L. SkewBotNorm=SkewNorm($y_1$,average k=1:5,3)  (41)

R. SkewBotNorm=SkewNorm($y_2$,average k=1:5,3)  (42)

L. SkewLefNorm=SkewNorm($\bar{x}_1$,average k=1:5,4)  (43)

R. SkewLefNorm=SkewNorm($\bar{x}_2$,average k=1:5,4)  (44)

The method may also feature calculating box height, box width, box area, or box aspect ratio.

Box Height $$BoxHeight_{j,k} = \bar{y}_{j,k,1} - \bar{y}_{j,k,3} \quad (45)$$

Box Width $$BoxWidth_{j,k} = \bar{x}_{j,k,2} - \bar{x}_{j,k,4} \quad (46)$$

Box Aspect Ratio $$AspectRatio_{j,k} = \frac{BoxHeight_{j,k}}{BoxWidth_{j,k}} \quad (47)$$

Box Area $$BoxArea_{j,k} = BoxHeight_{j,k} \times BoxWidth_{j,k} \quad (48)$$

The method may also feature calculating conjugacy of eye movement or variance from perfect conjugacy of eye movement, such as, for example, $$Conj\,varXtop = \frac{\sum (\hat{x}_1)^2 - 0}{\sum \hat{x}_1}, \quad (57)$$

$$Conj\,varXrit = \frac{\sum (\hat{x}_2)^2 - 0}{\sum \hat{x}_2}, \quad (58)$$

$$Conj\,varXbot = \frac{\sum (\hat{x}_3)^2 - 0}{\sum \hat{x}_3}, \quad (59)$$

$$Conj\,varXlef = \frac{\sum (\hat{x}_4)^2 - 0}{\sum \hat{x}_4}, \quad (60)$$

$$Conj\,varYtop = \frac{\sum (\hat{y}_1)^2 - 0}{\sum \hat{y}_1}, \quad (61)$$

$$Conj\,varYrit = \frac{\sum (\hat{y}_2)^2 - 0}{\sum \hat{y}_2}, \quad (62)$$

-continued $$Conj\,varYbot = \frac{\sum (\hat{y}_3)^2 - 0}{\sum \hat{y}_3}, \quad (63)$$

$$Conj\,varYrit = \frac{\sum (\hat{y}_4)^2 - 0}{\sum \hat{y}_4}, \quad (64)$$

$$Conj\,CorrXYtop = \frac{\sum \hat{x}_1 \hat{y}_1}{\sum \hat{x}_1 - 1}, \quad (65)$$

$$Conj\,CorrXYrit = \frac{\sum \hat{x}_2 \hat{y}_2}{\sum \hat{x}_2 - 1}, \quad (66)$$

$$Conj\,CorrXYbot = \frac{\sum \hat{x}_3 \hat{y}_3}{\sum \hat{x}_3 - 1}, \quad (67)$$

$$Conj\,CorrXYlef = \frac{\sum \hat{x}_4 \hat{y}_4}{\sum \hat{x}_4 - 1}, \quad (68)$$

or variance x ratio top/bottom (conjugacy), variance y ratio top/bottom (conjugacy), variance x ratio left/right (conjugacy), or variance y ratio left/right (conjugacy).

In some instances, one or more of the L height, L width, L area, L varXrit, L varXlef, L varTotal, R height, R width, R area, R varYtop, R varXrit, R varXlef, R varTotal, Conj varX, Conj varXrit, Conj varXbot, Conj varXlef and Conj varYlef may be especially useful for demonstrating or detecting or assessing structural or non-structural traumatic brain injury such as, for instance, a concussion or blast injury.

In addition combining one of more of the above metrics using techniques including but not limited to "best subset", "LASSO", "random forest" or "logistic regression" may result in increased sensitivity of the eye tracking relative to use of only a single metric.

A standard deviation or p value of 0.25, 0.3, 0.4, 0.5, 0.75, 0.8, 0.9, 1.0, 1.5, 2.0, 2.5 or more may reflect that a subject has structural or non-structural traumatic brain injury such as, for instance, a concussion, subconcussion or blast injury. As such, the methods described herein may be used to detect concussion, subconcussion and blast injury and assess or determine the severity of the same.

In another aspect, a method for diagnosing a disease characterized by or featuring structural and non-structural traumatic brain injury in a subject may involve: tracking eye movement of at least one eye of the subject; analyzing eye movement of at least one eye of the subject; comparing eye movement of at least one eye of the subject to a normal or mean eye movement; and, optionally calculating a standard deviation or p value for eye movement of at least one eye of the subject.

In another aspect, methods for assessing or quantitating structural and non-structural traumatic brain injury or diagnosing a disease characterized by or featuring structural and non-structural traumatic brain injury in a subject may involve: tracking eye movement of at least one eye of the subject; collecting raw x and y cartesian coordinates of pupil position; normalizing the raw x and y Cartesian coordinates; and calculating one or more individual metric.

In some instances, eye movement of both eyes of the subject are tracked and analyzed. In some instances, both x and y coordinates of eye position for one or both eyes of a subject are collected for at least about 100, 500, 1,000, 5,000, 10,000, 50,000, 100,000, 200,000 or more eye positions. In instances where the eye movements of both eyes are tracked, the method may additionally feature sorting the data by eye.

In another aspect, a kit useful for detecting, screening for or quantitating structural and non-structural traumatic brain injury in a subject may include a device for tracking eye movement, one or more means for analyzing eye movement tracking data such as, for instance, an algorithm or computer program, and instructions. Processing eye movement observations, making measurements of eye movement observations, determining distributions of values measured and performing statistical tests may all be accomplished using suitable computer software that may be included in such a kit.

In another aspect, a computer system or computing device can be used to implement a device that includes the processor and the display, the eye movement/gaze tracker component, etc. The computing system includes a bus or other communication component for communicating information and a processor or processing circuit coupled to the bus for processing information. The computing system can also include one or more processors or processing circuits coupled to the bus for processing information. The computing system also includes main memory, such as a random access memory (RAM) or other dynamic storage device, coupled to the bus for storing information, and instructions to be executed by the processor. Main memory can also be used for storing position information, temporary variables, or other intermediate information during execution of instructions by the processor. The computing system may further include a read only memory (ROM) or other static storage device coupled to the bus for storing static information and instructions for the processor. A storage device, such as a solid state device, magnetic disk or optical disk, is coupled to the bus for persistently storing information and instructions.

The computing system may be coupled via the bus to a display, such as a liquid crystal display, or active matrix display, for displaying information to a user. An input device, such as a keyboard including alphanumeric and other keys, may be coupled to the bus for communicating information and command selections to the processor. In another implementation, the input device has a touch screen display. The input device can include a cursor control, such as a mouse, a trackball, or cursor direction keys, for communicating direction information and command selections to the processor and for controlling cursor movement on the display.

According to various implementations, the processes described herein can be implemented by the computing system in response to the processor executing an arrangement of instructions contained in main memory. Such instructions can be read into main memory from another computer-readable medium, such as the storage device. Execution of the arrangement of instructions contained in main memory causes the computing system to perform the illustrative processes described herein. One or more processors in a multi-processing arrangement may also be employed to execute the instructions contained in main memory. In alternative implementations, hard-wired circuitry may be used in place of or in combination with software instructions to effect illustrative implementations. Thus, implementations are not limited to any specific combination of hardware circuitry and software.

According to various embodiments, tracking eye movement may be performed using any suitable device such as, for example, an Eyelink® 1000 binocular eye tracker (500 Hz sampling, SR Research). The suitable device, i.e. the eye tracker, may be stationary or portable. The eye tracking movement samples may be obtained at any suitable frequency, such as for instance, 10 Hz to 10,000 Hz or more. The subject may be positioned an appropriate distance from the device, such as, for example, 10, 20, 30, 40, 50, 55, 60, 70, 80, 90 cm or more, or even a meter or more from the device screen. In some instances, the subject's head may be stabilized, such as, for instance by using a chinrest or similar stabilizing mechanism. The subject may be seated or reclining. Preferably, the presentation monitor of the device is adjusted so as to substantially match the subject's gaze direction. The tracking eye movement may be performed for a total of, for example, 30, 60, 90, 120, 150, 180, 200, 220, 240, 270, 300, 330, 360, 400, 450, 500 seconds or more, or for 5, 10, 15, 20, 25, 30, 45, 60, or 90 minutes or more. As such, according to the methods provided, 1,000, 5,000, 10,000, 20,000, 25,000, 50,000, 75,000, 100,000, 150,000, 200,000, 250,000, 300,000 or more samples of eye position may be obtained. Similarly, the tracking eye movement may be performed using a video oculography device, such as, for instance, goggles, or using a web-cam based tracking system.

According to various embodiments, analyzing eye movement may be performed by any suitable means. In some instances, a stimulus and an analysis stream are provided that allows interpreting raw eye position data. In some instances, an algorithm may be provided for looking at pupil position directly thereby yielding information about ocular motility. Preferably, a device is adapted into a novel mobile system that may analyze eye movement close in time or substantially concurrent to the eye movement itself.

According to various embodiments, eye movement may be tracked in response to a visual stimulus. In some instances, the visual stimulus may be, for instance, a video such as a music video that may move, for instance clockwise, along the outer edge, of a computer monitor. In some instances, such a video may be provided starting at the upper or lower, left or right hand corners, of a screen. The visual stimulus such as a video, e.g. a music video, may be provided in a substantially square aperture with an area of approximately 10, 12, 14, 16, 18, 20, 25, or degrees, for example, approximately 1/10, 1/8, 1/6, 1/5, 1/4, 1/3, 1/2 of the size of the screen or so. The visual stimulus, such as, for example a music video, may play substantially continuously during the eye movement tracking, and it may in some instances move across the screen at a relatively or substantially constant speed. For instance, such a visual stimulus, for instance, a music video may cover each edge of a monitor in about 2, 5, 10, 15, 20, 30, 45 or 60 seconds or so. Therefore, in some instances, a full cycle may take, for instance, 10, 20, 30, 40, 50, 60, 75, 100, 120, 150, 180 seconds or so. Multiple cycles of such a visual stimulus, for instance a music video may be played, for instance, one, two, three, four, five, six, seven, eight, nine, ten, twelve, fifteen, twenty or more full cycles. As such, the visual stimulus may be provided, the eye movement may be tracked, in effect, in some instances the video may be played for a total of, for example, 30, 60, 90, 120, 150, 180, 200, 220, 240, 270, 300, 330, 360, 400, 450, 500 seconds or more. In instances where the visual stimulus is in the form of a video, a countdown video may be played in the starting position for, for instance, 5, 10, 15, 20, 25, or 30 seconds or more before beginning the visual stimulus, e.g. video, to provide subjects sufficient time to orient to the visual stimulus. Likewise, the visual stimulus, for instance a video, may be continued for an addition 2, 5, 10, 15, 20, 30, 45 or 60 seconds or so after the eye movement tracking is performed to reduce or substantially avoid boundary effects. The same result could be obtained by having the visual stimulus moving over any distance x relative to any amount of time t. The ideal stimulus would move however in the both the x and y Cartesian planes to optimize the assessment capability of the method.

Tracking eye movement may feature generating figures substantially resembling boxes that reflect the trajectory traveled by the visual stimulation, such as when it moves across a screen. In healthy controls, these figures substantially resembling boxes may look like, for instance, substantially equilateral rectangles or squares, reflecting the trajectory traveled by the visual stimulus across a screen. In instances of structural and non-structural traumatic brain injury, neurological damage or increased intracranial pressure, such figures may not substantially resemble a box, a rectangle or a square. In fact, in some instances, the cranial nerve having reduced or impaired function or conduction may be identified. In some instances, the figures generated that reflect the trajectory traveled by the visual stimulation may demonstrate abnormal distribution of or absence of normal plotting pairs in particular areas. Increased variability along the y-axis may for example reflect cranial nerve II dysfunction. Decreased variability along the y-axis, or decreased height to width ratio may reflect CN III dysfunction. Increased height to width ratio may reflect CN IV or VI dysfunction. The height of the box may be mathematically determined by assessing the position of the pupil as the video traverses the top and bottom of the presented visual stimulus. This "actual" height may be different from the perceived height mathematically, since the perceived height can represent aberrant pupillary motion due to the patient's ocular motility dysfunction. The integrity of the box walls may also be indicative of other types of dysfunction. Both cranial nerve palsies and mass effect may cause defects in box trajectory. CN III defects may impact the top and/or bottom of the box. CN VI palsies may impact the sides of the box.

Eye movement may also be tracked without using a moving stimulus. It is possible to assess eye movement without having the stimulus move at all, but by assessing the x, y coordinates over times during naturalistic viewing. For example, eye movement may be tracked during television watching or live viewing of an environment without a specific viewing apparatus such as a monitor or screen.

DETAILED DESCRIPTION

Before the present methods are described, it is to be understood that this invention is not limited to particular methods and experimental conditions described, as such methods and conditions may vary. It is also to be understood that the terminology used herein is for purposes of describing particular embodiments only, and is not intended to be limiting, since the scope of the present invention will be limited only by the appended claims. As used in this specification and the appended claims, the singular forms "a", "an", and "the" include plural references unless the context clearly dictates otherwise. Thus, for example, references to "the method" includes one or more methods, and/or steps of the type described herein and/or which will become apparent to those persons skilled in the art upon reading this disclosure and so forth in their entirety.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference I their entireties.

Definitions

The terms used herein have the meanings recognized and known to those of skill in the art, however, for convenience and completeness, particular terms and their meanings are set forth below.

"Subject" or "patient" refers to a mammal, preferably a human, undergoing treatment or screening for a condition, disorder or disease such as, for instance, any condition characterized by or featuring disconjugate gaze or strabismus.

By "assessing or quantitating structural and non-structural traumatic brain injury" is meant identifying, diagnosing, or determining the severity a traumatic brain injury such as, for instance, concussion, subconcussion or blast injury.

By "localizing a central nervous system lesion" is meant in some instances determining information that may predict a likely position of a lesion, for instance, determining the side of the body, for instance, left or right, where a lesion may likely be located within the central nervous system. In other instances, "localizing a central nervous system lesion" may mean determining a particular fossa or compartment, such as, for instance, a fascia compartment or brain ventricle in which a lesion is likely located within the central nervous system.

By "having eye movement of a first eye that is significantly different from eye movement of a second eye" is meant displaying eye movement in a first eye over 5, 10, 25, 50, 100, 1,000, 5,000, 10,000 or more observations, tracked with at least x, y coordinate positions, that is at least 5%, 10%, 15%, 20%, 25%, 30%, 40%, 50%, 75%, or 100% or more variant compared to the corresponding eye movement observations tracked from the second eye. The 5%, 10%, 15%, 20%, 25%, 30%, 40%, 50%, 75%, or 100% or more variant may be calculated or observed either numerically or graphically. Alternatively, "having eye movement of a first eye that is significantly different from eye movement of a second eye" is meant displaying eye movement in a first eye over 5, 10, 25, 50, 100, 1,000, 5,000, 10,000 or more observations, tracked with at least x, y coordinate positions, that, when graphically displayed in a scatterplot as described herein, is at least 5°, 10°, 15°, 20°, 25°, 30°, 40°, 50°, 60°, 75° or 90° or more variant compared to the corresponding eye movement observations tracked and graphically displayed on a scatterplot as described herein from the second eye.

Eye movement tracking for neuropsychiatric and brain injury research (Heitger, et al., *Brain,* 2009; 132: 2850-2870; Maruta, et al., *J Head Trauma Rehabil.,* 2010; 25: 293-305) has been performed for nearly 30 years and can evaluate smooth pursuit, saccades, fixation, pupil size and other aspects of gaze. Spatial calibration of the eye tracker is generally performed for each individual being tracked. With calibration, the eye-tracker measures the relative position of pupil and corneal reflection for a period of about 400-800 ms while the subject looks at a target or targets of known position to generate meaningful spatial coordinates during subsequent pupil movement. The process of spatial calibration implies relatively preserved neurologic function because it requires that the subject is able to follow commands and look at specific points.

The process of spatial calibration may mask deficits in ocular motility. If there is a persistent and replicable weakness in movement of an eye, the camera may interpret the eye's ability to move in the direction of that weakness as the full potential range of motion in that direction due to the calibration process. In other words if the subject is directed to look at a position but consistently only moves halfway there, the calibration process may account for that when tracking subsequent eye movements and interpret movements to the halfway point as occurring at the full range of normal motion. If during calibration one eye only makes it half-way to the target, but the other eye is fully there, the camera may interpret both eyes as being together when one performs half the eye movement as the other. Thus binocular spatial calibration may preclude detection of disconjugate gaze unless each eye is calibrated separately using a dichoptic apparatus (Schotter, et al., PLoS One, 2012; 7: e35608).

The present invention may use a novel technique for non-spatially calibrated tracking performed while subjects watch a music video moving inside an aperture on a computer monitor. The aperture moves around the monitor periphery at a known rate so that the position of the pupil can be predicted at any given time based on the time elapsed since the start of the video. By using elapsed time, rather than spatial calibration, the method detects impaired ability to move one pupil relative to the other. Uncalibrated tracking not only does not compensate for impaired motility, but also can be used in patients who do not follow commands such as aphasics, foreign-language speakers, persistently vegetative individuals and small children. It can also be used on animals.

If the subject's eyes are positioned about 55 cm from the center of the 30×35 cm viewing monitor, the method and associated algorithm elicits pupil movement in a maximum range of about 15° in any direction from midposition, or approximately 30° total from top to bottom or side to side. Thus, in some instances, the method and associated algorithm may not require or assess the full range of ocular motility, nor the entire visual field. Use of a larger monitor, or one positioned closer to the subject would enable assessment of these.

The technique described herein differs from uncalibrated tracking using static stimuli for on-target and off-target fixations in a population of minimally conscious and persistently vegetative patients that have open eyes (Trojano, et al., J Neurol., 2012 (published online; ahead of print)). The moving images shown within an aperture that moves periodically allow assessing both coarse and fine eye movement characteristics in both controls and neurologically impaired subjects. Unlike other studies (Contreras, et al., Brain Res., 2011; 1398: 55-63; Contreras, et al., J Biol Phys., 2008; 34: 381-392; Maruta, et al., J Head Trauma Rehabil., 2010; 25: 293-305; Trojano, et al., J Neurol., 2012 (published online; ahead of print)) the present methods do not use saccade count or spatial accuracy which requires transformation of raw data by a series of scaling and rotating processes whose effectiveness depends on the ability of their subjects to follow precise commands reliably. The present methods also differ from gaze estimation, which requires either a fixed head position or multiple light sources and cameras to localize the pupil (Guestrin, et al., IEEE Trans Biomed Eng., 2006; 53: 1124-1133).

Video oculography is a relatively newer technique that uses infrared cameras mounted in goggles to track the center of the pupil's position as the eye moves. It has been demonstrated to be useful in screening for neurovestibular and labyrinthine dysfunction and most recently in distinguishing these from vertebrobasilar stroke (Newman-Toker, et al., Stroke, 2013; 44: 1158-1161). Video oculography generally relies on spatial calibration (Hong, et al., Behav Res Methods, 2005; 37: 133-138; Schreiber, et al., IEEE Trans Biomed Eng., 2004; 51: 676-679). The use of our non-calibrated stimulus algorithm with video oculography rather than a sole eye tracking camera might be an interesting subject for future study.

The methods described herein provide both sensitivity and specificity. Because so many different cortical functions are required for watching a video, any process impeding global cranial function or specific cranial nerve function will likely be revealed by the present methods. Tracking may be confounded in patients with a history of prior brain insult, who are intoxicated, or are under the influence of pharmacologic agents. Patients' cognitive abilities, attention span and distractibility will impact the quality of ocular motility data.

Binocular Eye Movement Monitoring

When the human brain is physiologically intact, the eyes move together with a conjugate gaze. Only by deliberate conscious effort can an individual overcome this mechanism (eg when they deliberately "cross" the eyes.) A failure of the eyes to move in complete synchrony is called disconjugate gaze.

Binocular tracking may be used to compare the non-spatially calibrated trajectory of one eye to the other. Subtle differences between the trajectories of the two eyes may be detected. These differences provide valuable information regarding the physiologic function or dysfunction of the movement of one eye relative to the other. In the absence of known structural ocular injury, such differences reflect physiologic differences in the function of the two sides of the brain. Since brain lesions due to stroke, trauma or concussion, tumors, demyelinating disease, hydrocephalus, degenerative disease, etc. are rarely completely symmetric, comparing the eye movement of one eye to the eye movement of the other eye may be used to either confirm the presence of a lesion, to differentiate the existence of a lesion from other more global factors that may affect a person's ability to participate in an eye tracking task, such as fatigue, intoxication, medications, drug abuse, malingering, or lack of willingness to participate in an eye tracking task.

Thus binocular tracking and directly comparing the trajectories obtained over time, rather than with spatial calibration, may be used to diagnose pathology and to distinguish between these diagnoses and global factors that may impact eye tracking. In addition to or instead of an eye tracking camera, a video oculography device such as goggles may be used to evaluate eye movements over time rather than with spatial calibration. The eye tracking device may also be located remotely and function via the internet or other visualization mechanism.

Computing System

A computing system according to the invention is described herein. Implementations of the observer matter and the functional operations described herein can be implemented in other types of digital electronic circuitry, or in computer software, firmware, or hardware, including the structures disclosed in this specification and their structural equivalents, or in combinations of one or more of them. The computer system or computing device 1000 can be used to implement a device that includes the processor 106 and the display 108, the eye movement/gaze tracker component 104, etc. The computing system 1000 includes a bus 1005 or other communication component for communicating information and a processor 1010 or processing circuit coupled to the bus 1005 for processing information. The computing system 1000 can also include one or more processors 1010 or processing circuits coupled to the bus for processing information. The computing system 1000 also includes main memory 1015, such as a random access memory (RAM) or other dynamic storage device, coupled to the bus 1005 for storing information, and instructions to be executed by the processor 1010. Main memory 1015 can also be used for storing position information, temporary variables, or other intermediate information during execution of instructions by the processor 1010. The computing system 1000 may further include a read only memory (ROM) 1010 or other static storage device coupled to the bus 1005 for storing static information and instructions for the processor 1010. A storage device 1025, such as a solid state device, magnetic disk or optical disk, is coupled to the bus 1005 for persistently storing information and instructions.

The computing system 1000 may be coupled via the bus 1005 to a display 1035, such as a liquid crystal display, or active matrix display, for displaying information to a user. An input device 1030, such as a keyboard including alphanumeric and other keys, may be coupled to the bus 1005 for communicating information and command selections to the processor 1010. In another implementation, the input device 1030 has a touch screen display 1035. The input device 1030 can include a cursor control, such as a mouse, a trackball, or cursor direction keys, for communicating direction information and command selections to the processor 1010 and for controlling cursor movement on the display 1035.

According to various implementations, the processes described herein can be implemented by the computing system 1000 in response to the processor 1010 executing an arrangement of instructions contained in main memory 1015. Such instructions can be read into main memory 1015 from another computer-readable medium, such as the storage device 1025. Execution of the arrangement of instructions contained in main memory 1015 causes the computing system 1000 to perform the illustrative processes described herein. One or more processors in a multi-processing arrangement may also be employed to execute the instructions contained in main memory 1015. In alternative implementations, hard-wired circuitry may be used in place of or in combination with software instructions to effect illustrative implementations. Thus, implementations are not limited to any specific combination of hardware circuitry and software.

Implementations of the observer matter and the operations described herein can be implemented in digital electronic circuitry, or in computer software, firmware, or hardware, including the structures disclosed in this specification and their structural equivalents, or in combinations of one or more of them. The observer matter described herein can be implemented as one or more computer programs, i.e., one or more modules of computer program instructions, encoded on one or more computer storage media for execution by, or to control the operation of, data processing apparatus. Alternatively or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate components or media (e.g., multiple CDs, disks, or other storage devices). Accordingly, the computer storage medium is both tangible and non-transitory.

The operations described herein can be performed by a data processing apparatus on data stored on one or more computer-readable storage devices or received from other sources.

The term "data processing apparatus" or "computing device" encompasses all kinds of apparatus, devices, and machines for processing data, including by way of example a programmable processor, a computer, a system on a chip, or multiple ones, or combinations of the foregoing. The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, implementations of the observer matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

Described herein are many specific implementation details, these should not be construed as limitations on the scope of any inventions or of what may be claimed, but rather as descriptions of features specific to particular implementations of particular inventions. Certain features described herein in the context of separate implementations can also be implemented in combination in a single implementation. Conversely, various features described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated in a single software product or packaged into multiple software products.

The Relationship of Aspect Ratio and Variance as Measures of the Signal.

When the (x, y) pairs are plotted to show the 'box plots,' they have been preprocessed because the absolute values of the raw data are of limited use since changes in the signal over time are most important. There are many ways to normalize data, including dividing by the mean, by the standard deviation, or by the variance. Furthermore, the standard deviation or variance can be computed for all the data at once or x can be normalized using the variance of x and y can be normalized using the variance of y. Any normalization procedure for periodic data likely includes subtracting the mean, so the signal can be plotted as signal change alternating around zero. All of these transformations are conventional and widely used in data analysis by those of ordinary skill in the art. The details depend on the question being asked and the type of modeling or statistical testing being used.

In creating the box plots described herein, the raw data is preprocessed as follows: for the x (horizontal) and y (vertical) vectors independently, the mean is subtracted and divided by the standard deviation (which is the square root of the variance). This puts all the data in the same relative frame (zero-mean, max and min about 1 and −1). This is the reason the boxes look square (even if the stimulus presentation monitor is not square).

Figure 4:
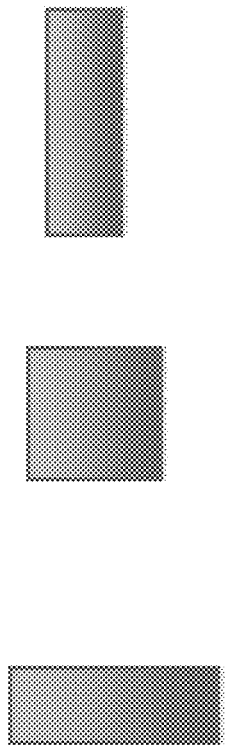
FIG. 4 is a diagram showing the impact of variance on aspect ratio.

This means that 'long' and 'short' sides are reflecting relative variability. If the variability is high, the denominator is high and the measure value low. So, for example, if the variability of the horizontal (x) data is high relative to the variability of the vertical (y) data, the horizontal aspect of the box will be relatively smaller, and the result will be a tall skinny box (higher aspect ratio). Conversely, if the variability of the vertical (y) data is high relative to the variability of the horizontal (x) data, the vertical range will be reduced and the result will be a short fat box (lower aspect ratio) (FIG. 4).

Thus, particular implementations of the observer matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

Conjugacy of Eye Movement

The methods described herein may identify strabismus. In a population of 14,006 consecutive patients examined at a pediatric eye clinic in Rome, 2.72% demonstrated either A or V-pattern strabismus (Dickmann, et al., *Ophthalmic Epidemiol.*, 2012; 19: 302-305). A-pattern was associated with a greater prevalence of neurological impairment, hydrocephalus and meningomyelocele, while those with V-pattern exhibited a greater prevalence of craniosynostosis and malformative syndromes (Dickmann, et al., *Ophthalmic Epidemiol.*, 2012; 19: 302-305). Delays in treatment of strabismus onset following binocular vision maturation may be associated with permanent disruption of stereopsis and sensory fusion (Fawcett, *Curr Opin Ophthalmol.*, 2005; 16: 298-302).

Given the relatively low prevalence of strabismus, the methods described herein are useful for the rapid automated assessment of acquired disconjugacy. Such disconjugacy may be due to neurologic causes including trauma, hydrocephalus, demyelination, inflammation, infection, degenerative disease, neoplasm/paraneoplastic syndrome, metabolic disease including diabetes, or vascular disruption such as stroke, hemorrhage or aneurysm formation. Disconjugacy may also be due to ophthalmologic causes such as conjunctivitis, ophthalmoplegia, ocular injury or other diseases. The methods described herein may feature assessing conjugacy or disconjugacy of eye movement in correlation with structural and non-structural traumatic brain injury, including concussion or blast injury.

Structurally and Non-Structurally Brain Injured Subjects

A purpose of the prospective observational study described herein was to quantitate differences in eye tracking of structurally and non-structurally brain injured subjects relative to non-brain but bodily injured and healthy non-injured controls to identify the eye tracking parameters associated with structural and non-structural injury. Another purpose was to identify a correlation between impaired eye tracking and clinical neurologic functioning. Eye tracking and clinical concussion assessments were performed on 44 injured subjects, and eye tracking was performed only on 31 healthy normal controls. 51 eye tracking parameters were assessed in each patient. 10 parameters showed statistically significant differences between negative controls (healthy normal people and corporally injured trauma patients) and both positive controls (patients with structural brain injury) and patients with non-structural brain injury. 8 additional parameters showed statistically significant differences between negative controls (healthy normal people and corporally injured trauma patients) and patients with either structural or non-structural brain injury. 10 of the eye tracking measures showed statistically significant correlation between SCAT or SAC scores, demonstrating that these eye tracking parameters correlated with a validated clinical outcome measure.

In order to assess ocular motility including the function of cranial nerves III, IV, and VI and associated nuclei, a novel technique for automated eye movement tracking was developed using temporal rather than spatial calibration. The position of the pupil is predicted based on time elapsed since the start of the video rather than spatial calibration, enabling detection of impaired ability to move the pupil relative to normal controls or the opposite eye. Temporal calibration offers the additional advantage of utility to populations that may not be willing or able to cooperate with calibration instructions such as young children, foreign-language speakers, minimally conscious persons, or aphasics.

The data presented herein quantitates differences in eye tracking of structurally and non-structurally brain injured subjects relative to non-brain but bodily injured and healthy non-injured controls to identify the parameters associated with structural and non-structural injury. The data presented herein further establish a correlation between impaired eye tracking and clinical neurologic functioning.

General Definitions

Raw x and y cartesian coordinates of pupil position are collected and stored in a one-dimensional vector:

$$x_{i_1} \tag{1}$$

$$y_{i_1} \tag{2}$$

This data is normalized according to the following form:

$$\bar{x}_i = \frac{x_i - \text{Mean}(x)}{\sigma_x}, \tag{3}$$

$$\bar{y}_i = \frac{y_i - \text{Mean}(y)}{\sigma_y}, \tag{4}$$

Index i corresponds to an individual data point. The size of i depends on the eye tracking hardware capture frequency and the time of tracking. The data is then sorted by eye (j=1:2, left, right), cycle (current stimulus method features an aperture that moves around the computer screen for five cycles) (k=1:5, first, second, third, fourth, fifth) and box segment (l=1:4, top, right, bottom, left). Implicit, is that each j, k, l has its own data points, n, whose size is also governed by the hardware tracking frequency and time length.

$$\bar{x}_i \rightarrow \bar{x}_{j,k,l}, \tag{5}$$

$$\bar{y}_i \rightarrow \bar{y}_{j,k,l}, \tag{6}$$

Individual Metrics
Segment Mean $$\bar{x}_{j,k,l}, \tag{7}$$

$$\bar{y}_{j,k,l}, \tag{8}$$

Corresponds to the arithmetic average of all data points on each segment l for all j, k. The result is one number representing each segment l.

Median

Corresponds to the statistical median of all data points on each segment l for all j, k. The result is one number representing each segment l.

$$\tilde{\bar{x}}_{j,k,l}, \tag{9}$$

$$\tilde{\bar{y}}_{j,k,l}, \tag{10}$$

Segment Variance $$\text{Var}(\bar{x}_{j,k,l}), \tag{11}$$

$$\text{Var}(\bar{y}_{j,k,l}), \tag{12}$$

Corresponds to the statistical variance of all data points on each segment l for all j, k. The result is one number representing each segment l.

Specific Metrics $$L.\ \text{var}Ytop = \text{Var}(\bar{y}_{1,\text{average } k=1:5,1}) \tag{13}$$

$$R.\ \text{var}Ytop = \text{Var}(\bar{y}_{2,\text{average } k=1:5,1}) \tag{14}$$

$$L.\ \text{var}Xrit = \text{Var}(\bar{x}_{1,\text{average } k=1:5,2}) \tag{15}$$

$$R.\ \text{var}Xrit = \text{Var}(\bar{x}_{2,\text{average } k=1:5,2}) \tag{16}$$

$$L.\ \text{var}Ybot = \text{Var}(\bar{y}_{1,\text{average } k=1:5,3}) \tag{17}$$

$$R.\ \text{var}Ybot = \text{Var}(\bar{y}_{2,\text{average } k=1:5,3}) \tag{18}$$

$$L.\ \text{var}Xlef = \text{Var}(\bar{x}_{1,\text{average } k=1:5,4}) \tag{19}$$

$$L.\ \text{var}Xlef = \text{Var}(\bar{y}_{2,\text{average } k=1:5,4}) \tag{20}$$

$$L.\ \text{var}Total = \text{Average}(\text{Var}(\bar{x}_{1,\text{average } k=1:5}) + \text{Var}(\bar{y}_{1,\text{average } k=1:5})) \tag{21}$$

$$R.\ \text{var}Total = \text{Average } \sigma_{\bar{x}_{j,k,l}}, \tag{23}$$

$$\sigma_{\bar{x}_{j,k,l}}, \tag{24}$$

Corresponds to the statistical standard deviation of all data points on each segment l for all j, k. The result is one number representing each segment l.

Segment Skew $$\text{Skew}(\bar{x}_{j,k,l}) = \bar{x}_{j,k,l} - \tilde{\bar{x}}_{j,k,l}, \tag{25}$$

$$\text{Skew}(\bar{y}_{j,k,l}) = \bar{y}_{j,k,l} - \tilde{\bar{y}}_{j,k,l}, \tag{26}$$

Corresponds to the statistical skew (how far the mean is from the median) of all data points on each segment l for all j, k. The result is one number representing each segment l.

Specific Metrics $$L.\ \text{SkewTop} = \text{Skew}(\bar{y}_{1,\text{average } k-1:5,1}) \tag{27}$$

$$R.\ \text{SkewTop} = \text{Skew}(\bar{y}_{2,\text{average } k-1:5,1}) \tag{28}$$

$$L.\ \text{SkewRit} = \text{Skew}(\bar{x}_{1,\text{average } k-1:5,2}) \tag{29}$$

$$R.\ \text{SkewRit} = \text{Skew}(\bar{x}_{2,\text{average } k-1:5,2}) \tag{30}$$

$$L.\ \text{SkewBot} = \text{Skew}(\bar{y}_{1,\text{average } k-1:5,3}) \tag{31}$$

$$R.\ \text{SkewBot} = \text{Skew}(\bar{y}_{2,\text{average } k-1:5,3}) \tag{32}$$

$$L.\ \text{SkewLef} = \text{Skew}(\bar{x}_{1,\text{average } k-1:5,4}) \tag{33}$$

$$R.\ \text{SkewLef} = \text{Skew}(\bar{x}_{2,\text{average } k-1:5,4}) \tag{34}$$

Segment Normalized Skew $$SkewNorm(\bar{x}_{j,k,l}) = \frac{Skew(\bar{x}_{j,k,l})}{\sigma_{\bar{x}_{j,k,l}}}, \quad (35)$$

$$SkewNorm(\bar{y}_{j,k,l}) = \frac{Skew(\bar{y}_{j,k,l})}{\sigma_{\bar{y}_{j,k,l}}}, \quad (36)$$

Specific Metrics $L.$ SkewTopNorm=SkewNorm($\bar{y}_1$,average $k$=1:5,1) (37)

$R.$ SkewTopNorm=SkewNorm($\bar{y}_2$,average $k$=1:5,1) (38)

$L.$ SkewRitNorm=SkewNorm($\bar{x}_1$,average $k$=1:5,2) (39)

$R.$ SkewRitNorm=SkewNorm($\bar{x}_2$,average $k$=1:5,2) (40)

$L.$ SkewBotNorm=SkewNorm($y_1$,average $k$=1:5,3) (41)

$R.$ SkewBotNorm=SkewNorm($y_2$,average $k$=1:5,3) (42)

$L.$ SkewLefNorm=SkewNorm($\bar{x}_1$,average $k$=1:5,4) (43)

$R.$ SkewLefNorm=SkewNorm($\bar{x}_2$,average $k$=1:5,4) (44)

Box Height $$\text{BoxHeight}_{j,k} = \bar{y}_{j,k,1} - \bar{y}_{j,k,3} \quad (45)$$

Box Width $$\text{BoxHeight}_{j,k} = \bar{x}_{j,k,2} - \bar{x}_{j,k,4} \quad (46)$$

Box Aspect Ratio $$AspectRatio_{j,k} = \frac{BoxHeight_{j,k}}{BoxWidth_{j,k}} \quad (47)$$

Box Area $$\text{BoxArea}_{j,k} = \text{BoxHeight}_{j,k} \times \text{BoxWidth}_{j,k} \quad (48)$$

Conjugacy

The five cycles are averaged together to give one averaged cycle, rendering:

$$\bar{x}_{j,l}, \quad (49)$$

$$\bar{y}_{j,l}, \quad (50)$$

Then the data from the right eye is subtracted from the left eye to obtain a delta value:

$$\hat{x}_l = \bar{x}_{1,l} - \bar{x}_{2,l} \quad (51)$$

$$\hat{y}_l = \bar{y}_{1,l} - \bar{y}_{2,l} \quad (52)$$

Here x represents the left normalized raw x pupil position minus the right normalized raw x pupil position. l corresponds to the top, right, bottom and left segments of the box.

Variance (Conjugacy)

The variance here does not follow the traditional form of statistical variance. In the traditional form, the average of the data points is subtracted from the sum of individual data points. In this case, the average is forced to zero, thus inferring that the hypothetical control patient has perfect conjugacy (left and right eye move precisely together).

$$Conj\,varX = Var(\hat{x}) = \frac{\sum_{l=1}^{4}(\hat{x}_l)^2 - 0}{\sum_{l=1}^{4}\hat{x}_l}, \quad (53)$$

$$Conj\,varY = Var(\hat{y}) = \frac{\sum_{l=1}^{4}(\hat{y}_l)^2 - 0}{\sum_{l=1}^{4}\hat{y}_l}, \quad (54)$$

$$TotalVariance = Conj\,totVar = Var(\hat{x}) = Var(\hat{y}) \quad (55)$$

$$\quad (56)$$

$$CoVariance - Conj\,CorrXY = \frac{\sum_{l=1}^{4}\hat{x}_l\hat{y}_l}{\sum_{l=1}^{4}\hat{x}_l - 1}$$

Specific Metrics $$Conj\,varXtop = \frac{\sum(\hat{x}_1)^2 - 0}{\sum\hat{x}_1}, \quad (57)$$

$$Conj\,varXrit = \frac{\sum(\hat{x}_2)^2 - 0}{\sum\hat{x}_2}, \quad (58)$$

$$Conj\,varXbot = \frac{\sum(\hat{x}_3)^2 - 0}{\sum\hat{x}_3}, \quad (59)$$

$$Conj\,varXlef = \frac{\sum(\hat{x}_4)^2 - 0}{\sum\hat{x}_4}, \quad (60)$$

$$Conj\,varYtop = \frac{\sum(\hat{y}_1)^2 - 0}{\sum\hat{y}_1}, \quad (61)$$

$$Conj\,varYrit = \frac{\sum(\hat{y}_2)^2 - 0}{\sum\hat{y}_2}, \quad (62)$$

$$Conj\,varYbot = \frac{\sum(\hat{y}_3)^2 - 0}{\sum\hat{y}_3}, \quad (63)$$

$$Conj\,varYrit = \frac{\sum(\hat{y}_4)^2 - 0}{\sum\hat{y}_4}, \quad (64)$$

$$Conj\,CorrXYtop = \frac{\sum\hat{x}_1\hat{y}_1}{\sum\hat{x}_1 - 1}, \quad (65)$$

$$Conj\,CorrXYrit = \frac{\sum\hat{x}_2\hat{y}_2}{\sum\hat{x}_2 - 1}, \quad (66)$$

$$Conj\,CorrXYbot = \frac{\sum\hat{x}_3\hat{y}_3}{\sum\hat{x}_3 - 1}, \quad (67)$$

$$Conj\,CorrXYlef = \frac{\sum\hat{x}_4\hat{y}_4}{\sum\hat{x}_4 - 1}, \quad (68)$$

Variance x Ratio Top/Bottom (Conjugacy)

$$Conj\,varXtopbotRatio = \frac{Var(\hat{x}_1)}{Var(\hat{x}_3)} \quad (69)$$

Variance y Ratio Top/Bottom (Conjugacy)

$$Conj\ varYtopbotRatio = \frac{Var(\hat{y}_1)}{Var(\hat{y}_3)} \qquad (70)$$

Variance x Ratio Left/Right (Conjugacy)

$$Conj\ varXlefritRatio = \frac{Var(\hat{x}_4)}{Var(\hat{x}_2)} \qquad (71)$$

Variance y Ratio Left/Right (Conjugacy)

$$Conj\ varYlefritRatio = \frac{Var(\hat{y}_4)}{Var(\hat{y}_2)} \qquad (72)$$

The following example is set forth to provide those of ordinary skill in the art with a description of how to make and use the methods, kits and compositions of the invention, and are not intended to limit the scope thereof. Efforts have been made to insure accuracy of numbers used (e.g., amounts, temperature, etc.), but some experimental errors and deviations should be accounted for. Unless indicated otherwise, parts are parts by weight, molecular weight is average molecular weight, temperature is in degrees Centigrade, and pressure is at or near atmospheric.

EXAMPLE

Abstract

INTRODUCTION: Objective diagnosis of concussion remains a challenge. Eye movements tracked at a very high frequency (~500 Hz) can detect abnormalities that last only a fraction of second. We mathematically converted abnormalities in eye movements related to concussion into a model that predicts the probability of being concussed in a pediatric patient population.

METHODS: This prospective case-control study recruited concussed and healthy control children from a concussion referral center. Eye movements were recorded while children watched a 220 second video clip as it rotated clockwise around the periphery of a 17"-viewing monitor. The pupils' raw coordinates were processed to obtain metrics that included measures from each eye separately and from both eyes together. Concussed patients were also evaluated clinically by performing convergence tests.

RESULTS: There were 32 age and gender matched subjects in each group (ages 4-21; mean 13; p-value for age-matching=0.979). Eye tracking data was used to build an optimal model that predicts the probability of concussion as defined by the CDC. Accurate detection as demonstrated by an area under the curve of 0.85 (sensitivity of 72% and specificity of 84%) was achieved. Clinical identification of abnormal near point of convergence also correlated with eye tracking (AUC=0.81)

CONCLUSION: Eye tracking correlates with clinical evaluations of convergence and can be used as a diagnostic tool for concussion in a pediatric concussion referral center population.

Subject selection: Controls were siblings of children visiting the neurosurgery clinic. Inclusion criteria for cases were less than 22 years of age, intact ocular motility, vision correctable to within 20/500 bilaterally, ability to provide a complete ophthalmologic, medical and neurologic history, medications consumed within past 24 hrs, and concussion within past 3 years. Parents were asked to corroborate details of the above for children aged 4-17 years of age. Controls were selected for the study if they were less than 22 years of age and free of any neurologic problems.

Patients were excluded if they were noted to have a history of strabismus, diplopia, palsy of CN III, IV or VI, papilledema, optic neuropathy or other known disorder of CN II, macular edema, retinal degeneration, dementia or cognitive impairment, sarcoidosis, myasthenia gravis, multiple sclerosis or other demyelinating disease. Comatose and sedated individuals were excluded.

Pregnant individuals, prisoners, subjects who were missing eyes, not opening eyes, or wearing excessive mascara/false eyelashes were excluded from the study.

All trauma patients were recruited from a concussion referral center and were subject to same inclusion and exclusion criteria as controls except for recent head injury, consentable and able/willing to participate in the study.

All children underwent eye tracking as well as two tests for convergence:

Convergence blurry—is the point at which an object moving closer to the nose becomes blurry.

Convergence double—is the point at which an object moving closer to the nose becomes double.

Definition of concussion: For the purposes of assessing eye movement as a biomarker for concussion, we defined concussion according to CDC acute concussion evaluation tool[1] using the symptom checklist developed by Lovell and Collins.[2] Precisely, patients were labelled as concussed if there was a positive injury description with evidence of forcible direct/indirect blow to the head, plus evidence of active symptoms of any type and number related to the trauma (Total Symptom Score>0), with or without evidence of loss of consciousness (LOC), skull fracture or intracranial injury.

Eye tracking procedure: Subjects' eye movements were recorded with an SR Research Eyelink 1000 eye tracker while a 220-second video was played continuously within a square aperture moving around the perimeter of a 17" viewing monitor (aspect ratio 4:3) fixed 55 cm away from the patient. The video aperture size was approximately $\frac{1}{9}^{th}$ the area of the display monitor. The position of the eyes were obtained at 500 Hz with a stabilized chin rest to minimize head movement during the eye tracking session. All subjects were asked to take off their glasses when being tracked. The visual stimuli were Disney PG music videos (e.g. Lion King, Hercules, and Puss in Boots). The total visible span of the moving aperture was somewhat approximately 17° horizontally and 13° vertically from mid-position with a caveat that the subject may be viewing different portions of the aperture during each cycle. The first and last 10 seconds of each data set were discarded to yield 200 seconds of data, yielding 100,000 data points. Both, the afferent stimulus presentation and eye tracking was binocular. Subjects were not spatially calibrated to the tracker to enable independent analysis of each pupil position over time.

The eye tracking data was processed to yield 89 eye tracking metrics as discussed previously.[3]

Statistical analysis: Statistical analyses were carried out using Statistical Package for the Social Sciences (SPSS version 19, IBM Corporation, Armonk, N.Y.).

Selection of candidate eye tracking metrics: An age and gender balanced sample was drawn from the pool of cases and controls to build model. Descriptive statistics were calculated for age and gender. Eye tracking metrics were compared using Wilcoxon rank sum tests to identify the metrics that correlated with concussion. Since an ideal biomarker should be independent of age and gender, these metrics were tested using Wilcoxon rank sum tests to identify their correlation with gender and with spearman correlation to identify their association with age.

Development and validation of a predictive model for concussion: We used logistic regression to build a model correlating eyetracking metrics to presence or absence of concussion. A receiver operating curve analysis was then carried out for this model, and an optimal cut off was determined. The frequencies of true positive, true negative, false positive and false negative were then calculated to appraise the model accuracy. The model was externally validated in the subjects not used in building the model.

Development and validation of a predictive model for near point of convergence: In addition to serve as a diagnostic tool concussion, we also tested whether or not eye tracking correlates with abnormality in the near point of convergence, a common clinical diagnosis of vision in concussed population, used in athlete sideline assessment tools.[45] We identified candidate eye tracking metrics that significantly correlated with abnormality in near point of convergence (NPC>6 cm) using Wilcoxon rank sum tests. The parameters thus identified were used to build a model to predict the probability of having an abnormal near point of convergence. A receiver operating curve analysis was constructed to appraise model accuracy.

Results

A total of 56 pediatric patients with concussion and 83 pediatric controls underwent eye tracking prospectively. The cases were on average 22.4 weeks (range: 0-109 weeks) out from injury.

Figure 7:
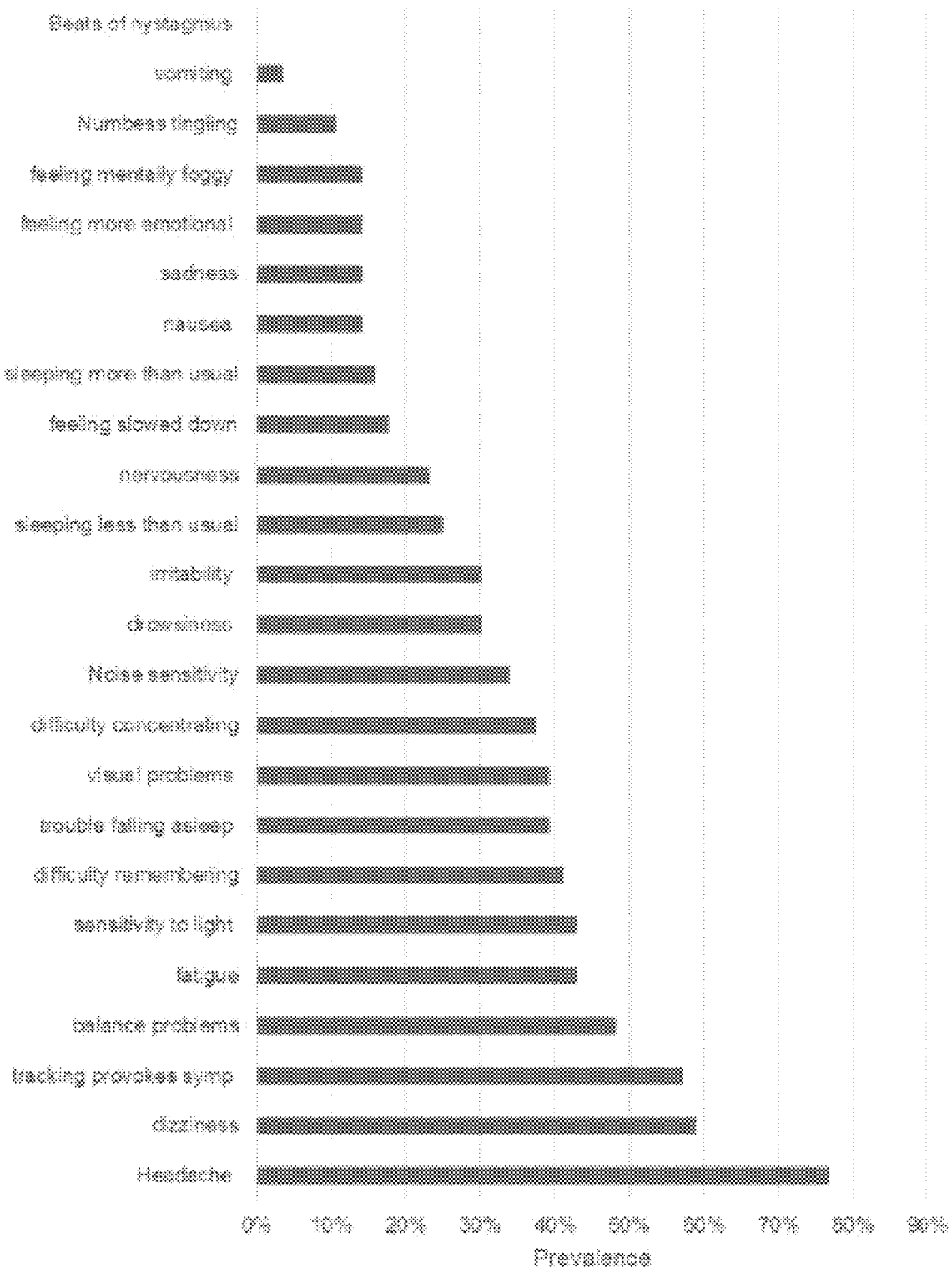
FIG. 7: is a bar graph showing prevalence of different symptoms in concussed patients
Figure 8:
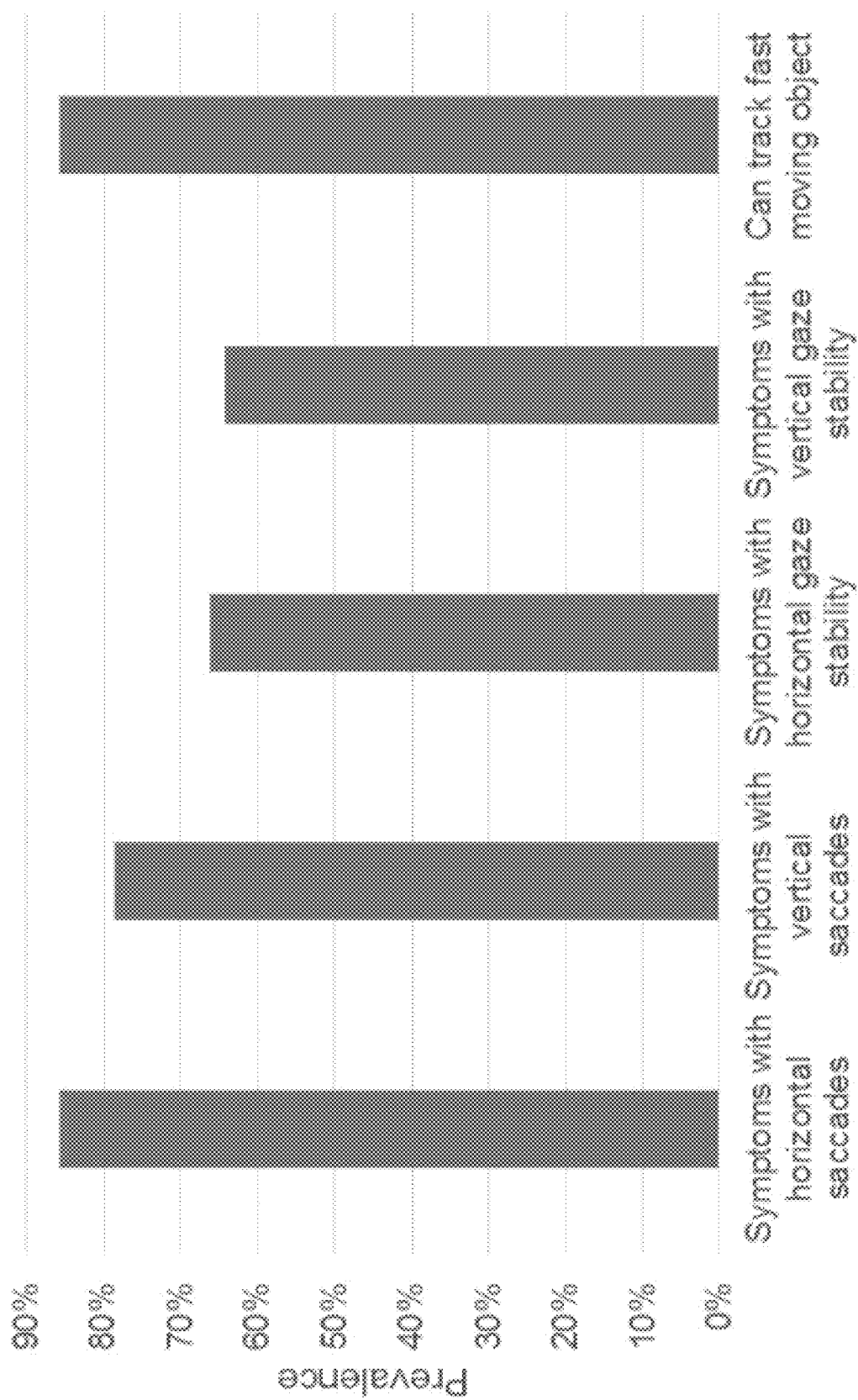
FIG. 8 is a bar graph showing prevalence of different signs in patients with concussion
Figure 9:
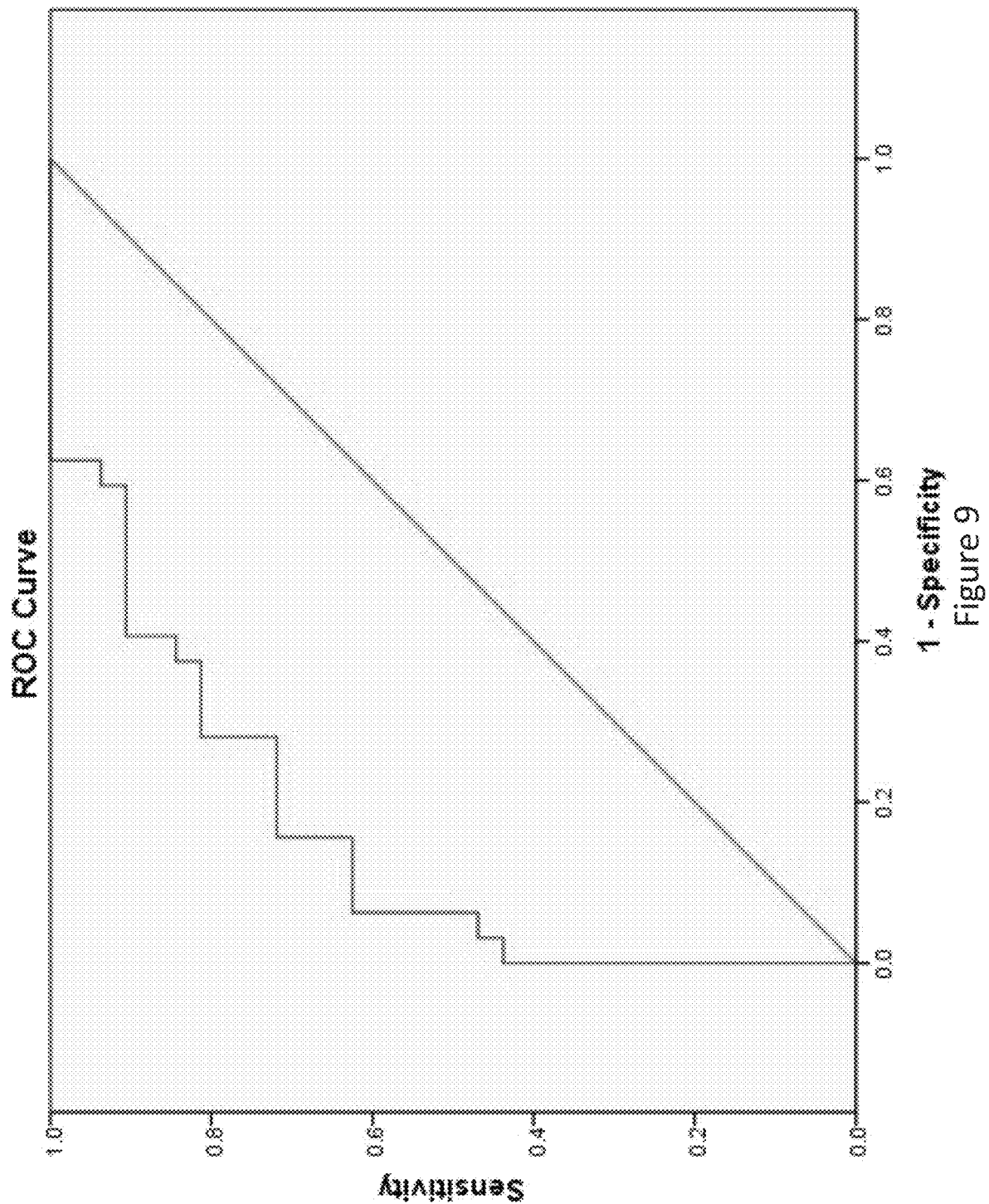
FIG. 9 is a receiver operating curve for eyetracking as a method of diagnosing concussion in the balanced sample of 32 patients and 32 control subjects. The area under the curve was 0.854.
Figure 10:
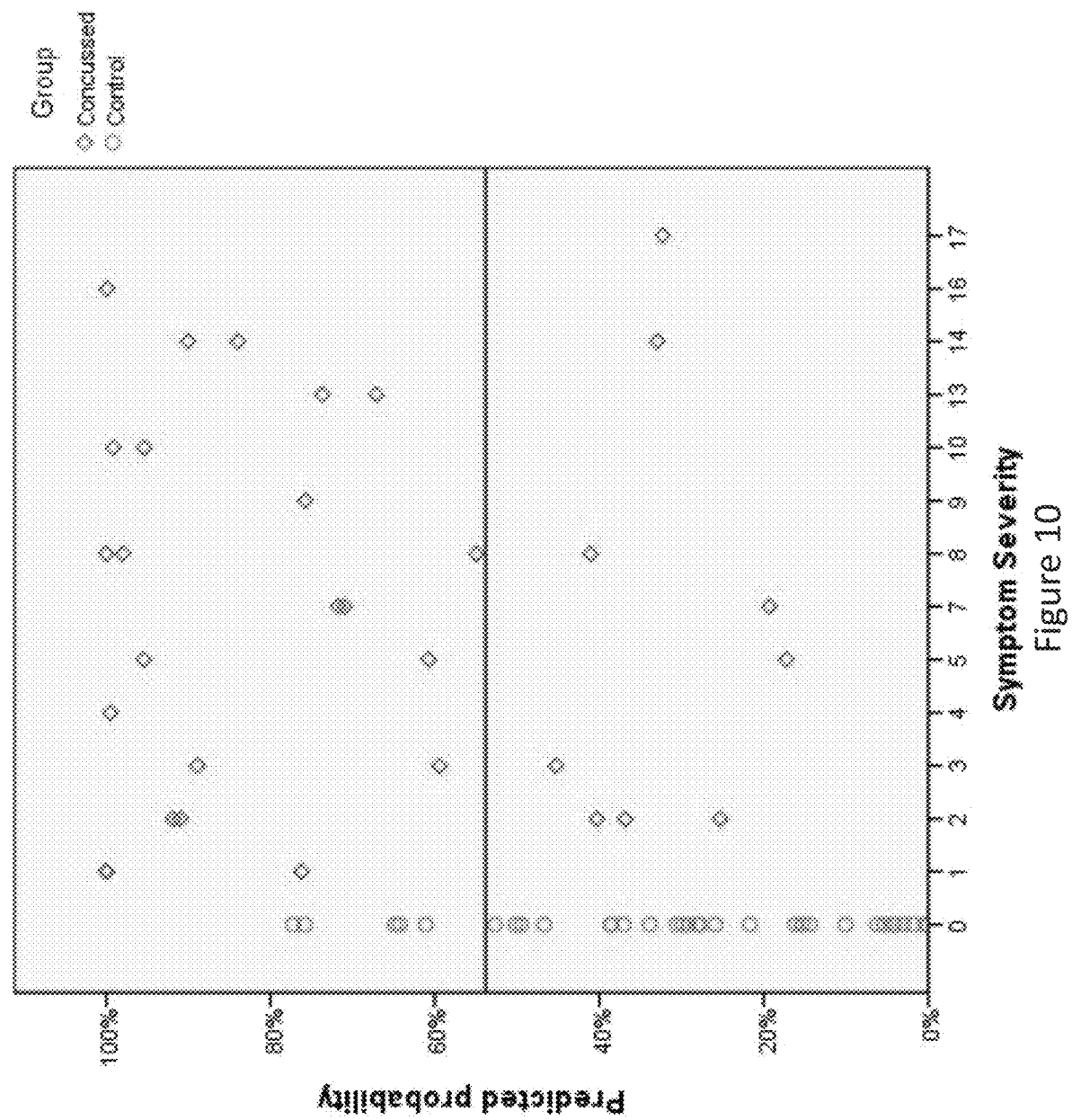
FIG. 10 is a scatter plot showing the predicted probability of concussion for cases and controls in the balanced sample. Concussed patients are identified by blue rhombus while controls are identified by green circles. The solid black line indicates the model cutoff, above which model will classify subject as concussed.

The symptom severity score is ranked out from 1 to 22. The data ranged from 1-17 indicating the most severe score was never reached in this population. FIG. 7 displays the prevalence of different symptoms, while FIG. 8 displays the prevalence of different signs in the concussed group. Headache was the most common symptom and was present in 76.8% (43) of the cases, 58.9% had dizziness, 14.3% (8) cases failed to track a fast moving object, and in 57.1% tracking provoked symptoms. 85.7% cases had symptoms with horizontal saccades, and 78.6% had symptoms with vertical saccades.

To balance age and gender in both groups, a balanced sample of 32 cases and 32 controls was obtained to create model. The descriptive statistics for balanced sample are given in Table 1 for age and in Table 2 for gender. The groups didn't differ in ages (p-value=0.979). Eye tracking metrics that significantly correlated with concussion are listed in Table 3. These metrics didn't correlate significantly with gender, or had a strong association with age.

We then built a logistic regression model that correlated eye tracking metrics to the state of being concussed. The metrics in this model are listed in Table 4 (FIG. 5). Interestingly, the model included the measures from both eyes and two measures of conjugacy.

We then performed receiver operating characteristic (ROC) curve analysis for the probability of being concussed predicted by the model built to the state of being concussed according to CDC criteria. The area under the receiver operating curve was 87.2% with a 95% confidence interval of 81.6%-92.7%. FIG. 1 displays an ROC. The cut-off point selected by the maximum of the Youden Index (sensitivity+ specificity=1), with the model having an accuracy of 80.6% with a sensitivity of 80.8% and specificity of 80.4% at this cut-off. The frequencies of true and false positives and negatives are given in Table 5.

Figure 11:
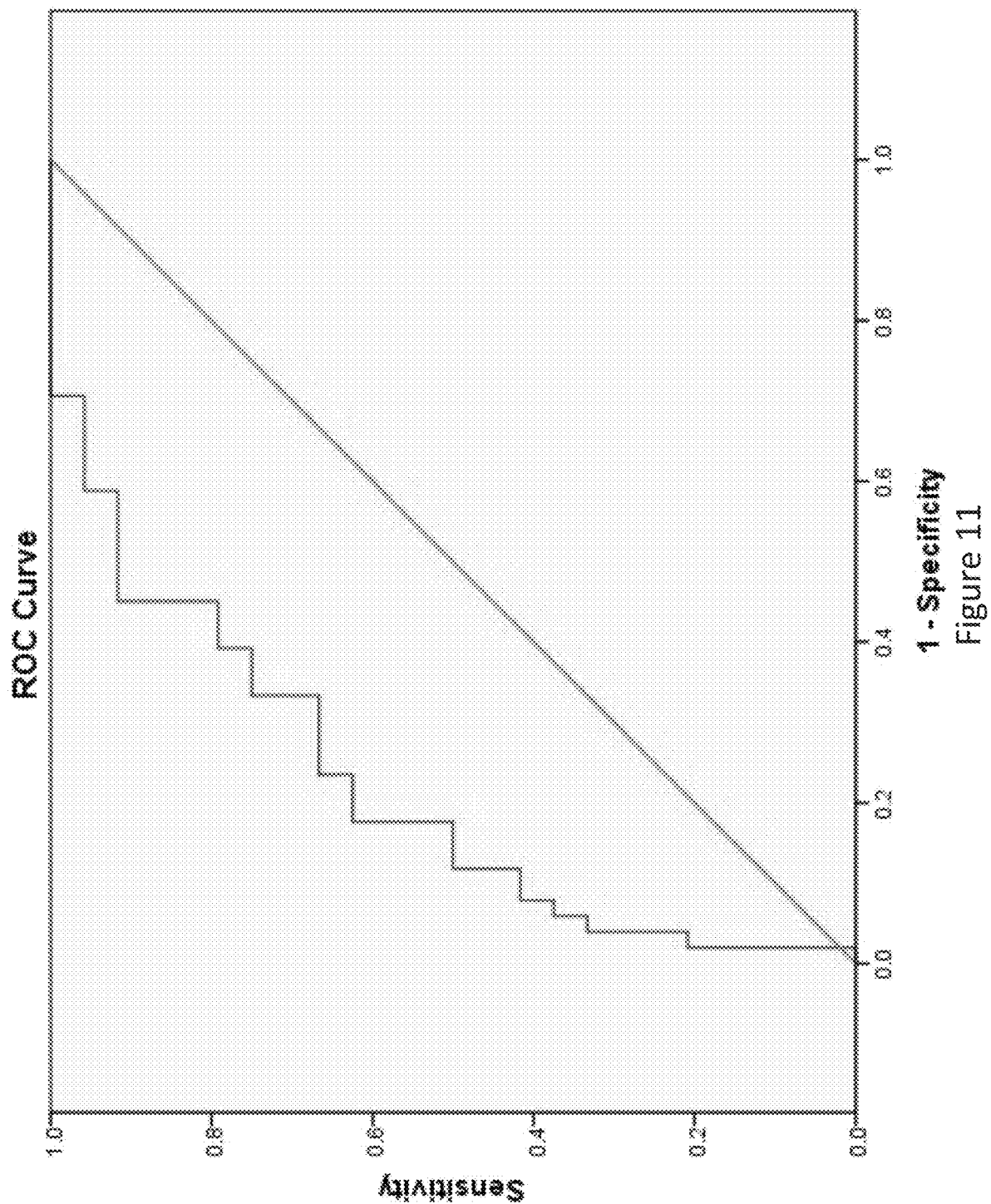
FIG. 11 is a receiver operating curve for eyetracking as a method of diagnosing concussion in a cross-validation sample of 24 patients and 51 control subjects. The area under the curve was 0.789.
Figure 12:
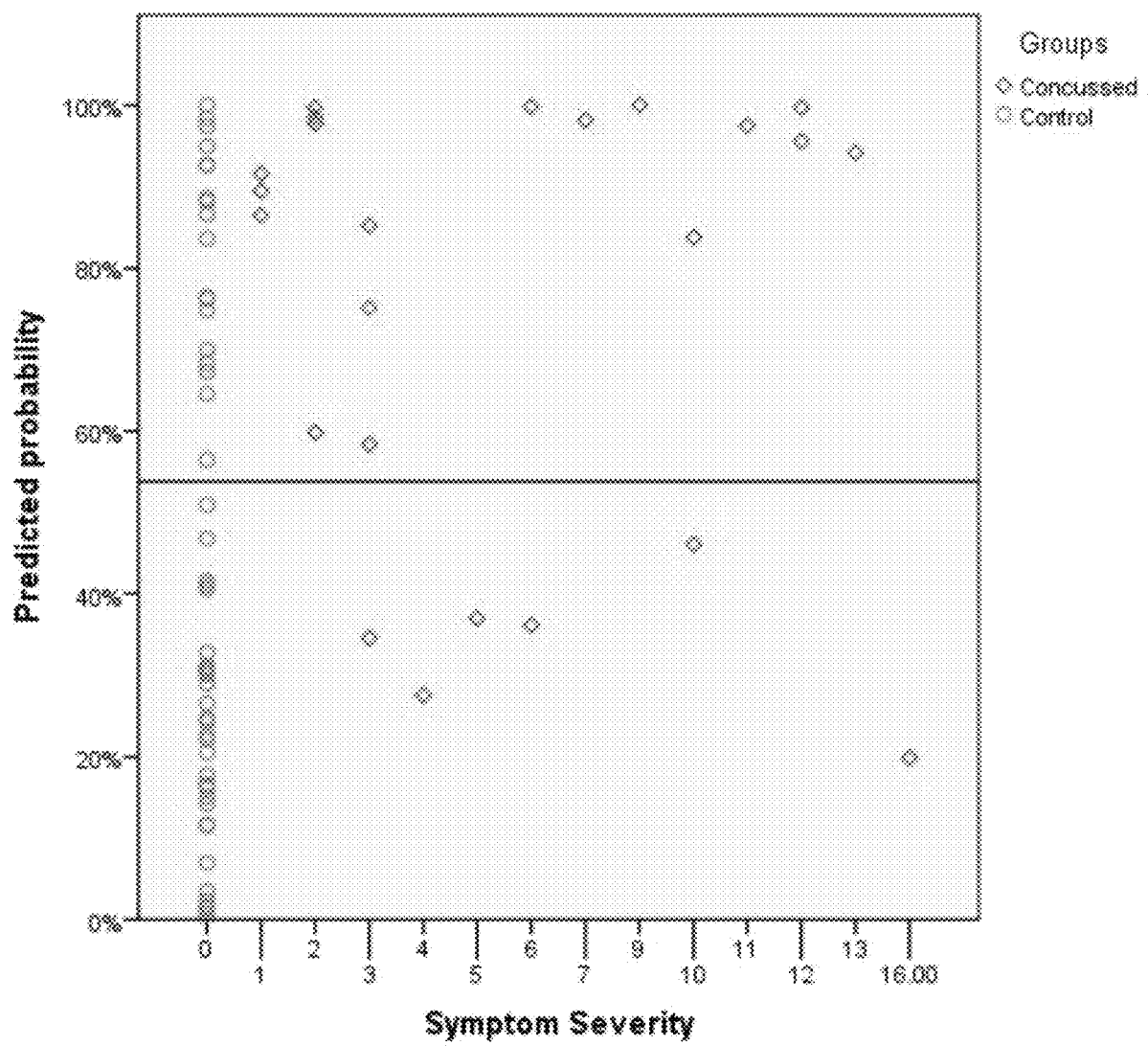
FIG. 12 is a scatter plot showing the predicted values for cases and controls in the cross-validation sample. Concussed patients are identified by blue rhombus while controls are identified by green circles. The solid black line indicates the model cutoff, above which model will classify subject as concussed.

The model was validated in population of 24 cases and 51 controls, the descriptive statistics of which listed in Table 6 for age and in Table 7 (FIG. 6) for gender. The receiver operating curve analysis yielded an area under the curve of 0.789 in this external population. FIG. 11. Table 8 displays the frequencies of true and false positives and negatives in external population.

Figure 13:
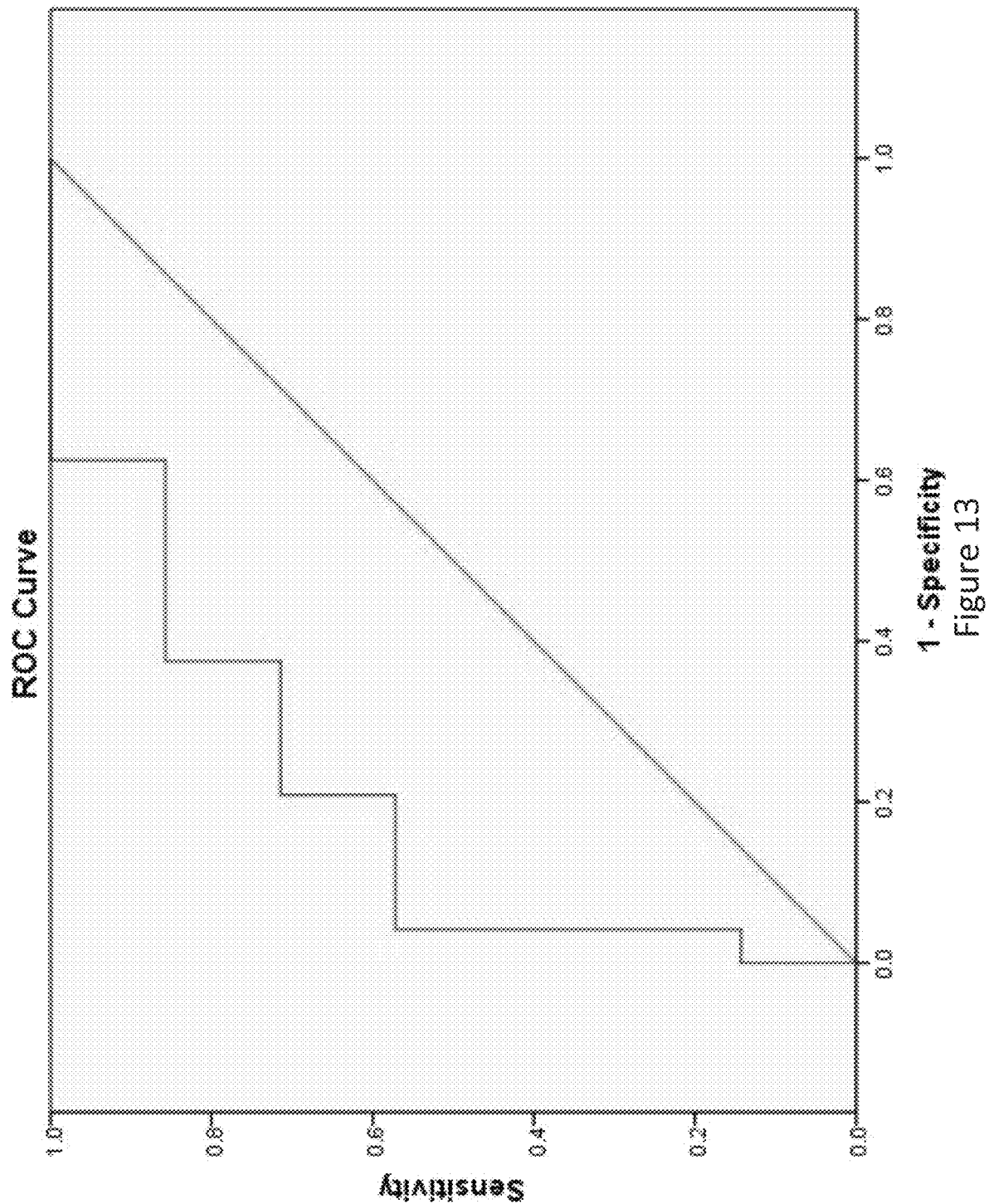
FIG. 13 is a receiver operating curve for eyetracking as it correlates to abnormality in near point of convergence (as defined by NPC>6 cm) in 32 concussed subjects. The area under the curve was 0.81.

Correlation of eye tracking with abnormality in near point of convergence: We also tested whether eye tracking correlates with near point of convergence and found right_velBot_value and conj_velRit_value to be a significant predictor of abnormal near point of convergence. A model built using these parameters to classify the cases based on their near point of convergence status achieved a specificity of 95.8% and a sensitivity of 57.1%. A receiver operating curve analysis indicated an area under the curve of 0.81. See FIG. 13.

Similarity in adult and pediatric eye tracking metrics: We compared the eye tracking metrics to previously published eye tracking metrics in adult population[1] and found six eye tracking metrics (conj_varXbot_value, left_distBot_value, left_distLef_value, left_varYtop_value, right_distBot_value, right_distRit_value) that were significant for both adult and pediatric population. This indicates that eye tracking metrics related concussion are strongly conserved in adult ER and pediatric concussion referral center populations.

TABLE 1

Descriptive statistics for age.
Statistics

| | | Age Symptom | | Gender Symptom | |
|---|---|---|---|---|---|
| | | .00 | 1.00 | .00 | 1.00 |
| N | Valid | 32 | 32 | 32 | 32 |
| | Missing | 0 | 0 | 0 | 0 |
| Mean | | 13.406250 | 13.437500 | .5313 | .5313 |
| Std. Error of Mean | | .8482185 | .8363437 | .08963 | .08963 |
| Median | | 13.500000 | 13.500000 | 1.0000 | 1.0000 |
| Mode | | 11.0000 | 12.0000 | 1.00 | 1.00 |
| Std. Deviation | | 4.7982482 | 4.7310744 | .50701 | .50701 |
| Variance | | 23.023 | 22.383 | .257 | .257 |
| Skewness | | −.275 | −.345 | −.131 | −.131 |
| Std. Error of Skewness | | .414 | .414 | .414 | .414 |
| Kurtosis | | −.831 | −.615 | −2.119 | −2.119 |
| Std. Error of Kurtosis | | .809 | .809 | .809 | .809 |
| Range | | 17.0000 | 17.0000 | 1.00 | 1.00 |
| Minimum | | 4.0000 | 4.0000 | .00 | .00 |
| Maximum | | 21.0000 | 21.0000 | 1.00 | 1.00 |
| Sum | | 429.0000 | 430.0000 | 17.00 | 17.00 |
| Percentiles | 10 | 5.600000 | 6.300000 | .0000 | .0000 |
| | 20 | 8.600000 | 9.000000 | .0000 | .0000 |
| | 25 | 11.000000 | 11.000000 | .0000 | .0000 |
| | 30 | 11.000000 | 11.000000 | .0000 | .0000 |
| | 40 | 11.200000 | 12.000000 | .0000 | .0000 |
| | 50 | 13.500000 | 13.500000 | 1.0000 | 1.0000 |
| | 60 | 16.000000 | 15.800000 | 1.0000 | 1.0000 |
| | 70 | 17.000000 | 17.000000 | 1.0000 | 1.0000 |
| | 75 | 17.750000 | 17.000000 | 1.0000 | 1.0000 |
| | 80 | 18.000000 | 18.000000 | 1.0000 | 1.0000 |
| | 90 | 19.700000 | 19.700000 | 1.0000 | 1.0000 |

TABLE 2

Frequencies of age:
Age

| | | Frequency Symptom | | Percent Symptom | | Valid Percent Symptom | | Cumulative Percent Symptom | |
|---|---|---|---|---|---|---|---|---|---|
| | | .00 | 1.00 | .00 | 1.00 | .00 | 1.00 | .00 | 1.00 |
| Valid | 4.0000 | 1 | 2 | 3.1 | 6.3 | 3.1 | 6.3 | 3.1 | 6.3 |
| | 5.0000 | 2 | | 6.3 | | 6.3 | | 9.4 | |
| | 6.0000 | | 1 | | 3.1 | | 3.1 | | 9.4 |
| | 7.0000 | 1 | 2 | 3.1 | 6.3 | 3.1 | 6.3 | 12.5 | 15.6 |
| | 8.0000 | 2 | | 6.3 | | 6.3 | | 18.8 | |
| | 9.0000 | 1 | 2 | 3.1 | 6.3 | 3.1 | 6.3 | 21.9 | 21.9 |
| | 11.0000 | 6 | 3 | 18.8 | 9.4 | 18.8 | 9.4 | 40.6 | 31.3 |
| | 12.0000 | 1 | 4 | 3.1 | 12.5 | 3.1 | 12.5 | 43.8 | 43.8 |
| | 13.0000 | 2 | 2 | 6.3 | 6.3 | 6.3 | 6.3 | 50.0 | 50.0 |
| | 14.0000 | 2 | 2 | 6.3 | 6.3 | 6.3 | 6.3 | 56.3 | 56.3 |
| | 15.0000 | | 1 | | 3.1 | | 3.1 | | 59.4 |
| | 16.0000 | 4 | 3 | 12.5 | 9.4 | 12.5 | 9.4 | 68.8 | 68.8 |
| | 17.0000 | 2 | 3 | 6.3 | 9.4 | 6.3 | 9.4 | 75.0 | 78.1 |
| | 18.0000 | 4 | 3 | 12.5 | 9.4 | 12.5 | 9.4 | 87.5 | 87.5 |
| | 19.0000 | 1 | 1 | 3.1 | 3.1 | 3.1 | 3.1 | 90.6 | 90.6 |
| | 20.0000 | 1 | 1 | 3.1 | 3.1 | 3.1 | 3.1 | 93.8 | 93.8 |
| | 21.0000 | 2 | 2 | 6.3 | 6.3 | 6.3 | 6.3 | 100.0 | 100.0 |
| | Total | 32 | 32 | 100.0 | 100.0 | 100.0 | 100.0 | | |

TABLE 3

Frequencies of Gender
Gender

| | | Frequency Symptom | | Percent Symptom | | Valid Percent Symptom | | Cumulative Percent Symptom | |
|---|---|---|---|---|---|---|---|---|---|
| | | .00 | 1.00 | .00 | 1.00 | .00 | 1.00 | .00 | 1.00 |
| Valid | Female | 15 | 15 | 46.9 | 46.9 | 46.9 | 46.9 | 46.9 | 46.9 |
| | Male | 17 | 17 | 53.1 | 53.1 | 53.1 | 53.1 | 100.0 | 100.0 |
| | Total | 32 | 32 | 100.0 | 100.0 | 100.0 | 100.0 | | |

TABLE 5

The Mann-Whitney U test was used to identify eye tracking metrics that were significantly associated with concussion

| Test Statistics | Mann-Whitney U | Wilcoxon W | Z | Asymp. Sig. (2-tailed) |
|---|---|---|---|---|
| left#distBot#value | 326 | 854 | −2.49745 | 0.012508988 |
| left#distLef#value | 327 | 855 | −2.48402 | 0.012990725 |
| right#distRit#value | 328 | 856 | −2.4706 | 0.013488799 |
| right#distBot#value | 331 | 859 | −2.43031 | 0.015085711 |
| right#skewRitNorm#value | 338 | 866 | −2.33632 | 0.019474321 |
| left#skewRit#value | 340 | 868 | −2.30947 | 0.020917489 |
| right#skewRit#value | 342 | 870 | −2.28262 | 0.022452988 |
| conj#varXbot#value | 345 | 873 | −2.24233 | 0.024939749 |
| left#skewRitNorm#value | 347 | 875 | −2.21548 | 0.026727109 |
| conj#varXtopbotRatio#value | 348 | 876 | −2.20205 | 0.027661548 |
| conj#varYtopbotRatio#value | 348 | 876 | −2.20205 | 0.027661548 |
| left#varYtop#value | 352 | 880 | −2.14834 | 0.031686389 |

TABLE 6

Correlation of eye tracking metrics with age. None of the eye tracking metric had a strong correlation with age.

| Spearman's rho, Correlation Coefficient | Age |
|---|---|
| conj#boxscore#value | −.389** |
| right#velLef#value | .304* |
| right#varXrit#value | −.291* |
| conj#boxscore5#value | −.280* |
| right#velRit#value | .280* |
| left#varXrit#value | −.268* |
| right#heightmedian#value | .262* |
| right#widthmedian#value | .262* |
| conj#varAspect#value | −.259* |
| right#areamedian#value | .259* |
| right#velTop#value | .259* |
| right#heightmean#value | .258* |
| right#distRit#value | −.257* |
| conj#velTop#value | −.255* |
| Age | 1.000 |

TABLE 8

Area Under the Curve
Test Result Variable(s): Predicted probability

| Area | Std. Error$^a$ | Asymptotic Sig.$^b$ | Asymptotic 95% Confidence Interval | |
|---|---|---|---|---|
| | | | Lower Bound | Upper Bound |
| .854 | .046 | .000 | .764 | .943 |

$^a$Under the nonparametric assumption
$^b$Null hypothesis: true area = 0.5

TABLE 9

Eye tracking model for convergence blurry (the point
at which an object moving closer to the nose becomes blurry)
Linear regression:

| Model | | t | Sig. | Coefficients[a] 95.0% Confidence Interval for B | |
|---|---|---|---|---|---|
| | | | | Lower Bound | Upper Bound |
| 7 | (Constant) | −1.160 | .252 | −11.722 | 3.159 |
| | left#velLef#value | −2.668 | .011 | −9.932 | −1.383 |
| | conj#varX#value | −.550 | .585 | −86.849 | 49.615 |
| | left#distRit#value | 4.989 | .000 | 1948.045 | 4588.569 |
| | right#areamedian#value | 3.905 | .000 | 1.807 | 5.661 |
| | conj#varYtopbotRatio#value | 2.496 | .016 | .018 | .166 |
| | left#heightmean#value | −2.033 | .048 | −8.728 | −.037 |
| | right#distLef#value | −2.011 | .051 | −2028.974 | 2.422 |

[a]Dependent Variable: convergence blurry

Based on these metrics we generated an equation to predict the value of CONVERGENCE_BLURRY.

The equation has a Pearson correlation of 0.781 (p-value<0.001) and a spearman correlation of 0.785 (p-value<0.001) with actual CONVERGENCE_BLURRY scores.

Correlation with break_double (the point at which an object moving closer to the nose is seen as double):

The break_double variable is difficult to model, since there are a lot of 1s 2s and 3s, and it appears to be ordinal instead of linear, but since break double has a strong correlation with CONVERGENCE_BLURRY, so we can use exact same equation for break double too, but with a spearman correlation of 0.554.

TABLE 10 showing correlations of the convergence blurry and convergence double model with each other.
Correlations

| | | | convergence blurry | break (double) | Pred convergenceblurry |
|---|---|---|---|---|---|
| Spearman's rho | convergence blurry | Correlation Coefficient | 1.000 | .752** | .815** |
| | | Sig. (2-tailed) | . | .000 | .000 |
| | | N | 55 | 54 | 55 |
| | break (double) | Correlation Coefficient | .752** | 1.000 | .554** |
| | | Sig. (2-tailed) | .000 | . | .000 |
| | | N | 54 | 54 | 54 |
| | Pred_convergenceblurry | Correlation Coefficient | .815** | .554** | 1.000 |
| | | Sig. (2-tailed) | .000 | .000 | . |
| | | N | 55 | 54 | 139 |

**Correlation is significant at the 0.01 level (2-tailed).

The invention claimed is:

1. A method for predicting abnormal eye convergence in a human or animal subject, the method comprising:
using an eye tracker having a camera to track pupil positions of a first eye and a second eye of the subject to generate eye tracking data for the subject as the subject watches a video, the eye tracking data including a plurality of data points for each of the first eye and the second eye;
temporally calibrating the eye tracker by independently predicting the pupil positions of the first eye and the second eye of the subject for each of the plurality of data points based on time elapsed since a start of the video;
calculating one or more metrics based on the eye tracking data, the one or more metrics comprising at least conjugacy metrics of both eyes of the subject;
determining a logistic regression model based on the one or more metrics; and
using at least the logistic regression model to compare movement of the first eye to the second eye and predict whether the subject has abnormal eye convergence.

2. The method as in claim 1, wherein generating the eye tracking data comprises: analyzing tracked eye movement; and comparing the tracked eye movement to a normal or mean eye movement.

3. The method as in claim 2, wherein generating the eye tracking data further comprises, after the comparing of the tracked eye movement, calculating a standard deviation or p value for the tracked eye movement as compared to the normal or mean eye movement.

4. The method as in claim 2, wherein the comparing of the tracked eye movement comprises comparing eye movement of said both eyes of the subject to eye movement of one or both eyes of one or more other subjects or controls.

5. The method as in claim 1, further comprising predicting whether a brain injury has occurred in the subject, based on the prediction of whether the subject has abnormal eye convergence.

6. The method as in claim 5, wherein predicting whether the brain injury has occurred comprises predicting whether a concussion has occurred by performing a receiver operating curve analysis of the logistic regression model to determine a cut off, and wherein the logistic regression model correlates the one or more metrics with the concussion based on the cut off.

7. The method as in claim 1, wherein eye movement is tracked for at least 40 seconds.

8. A system for predicting abnormal eye convergence in a human or animal subject, the system comprising:
- an eye tracking camera configured to track eye movement of the subject while the subject watches a video; and
- a processor coupled with the eye tracker having a camera and containing program instructions that, when executed, cause the processor to:
- process the tracked eye movement to generate eye tracking data for a first eye and a second eye, the eye tracking data including a plurality of data points for each of the first eye and the second eye;
- temporally calibrate the eye tracker by independently predicting pupil positions of the first eye and the second eye for each of the plurality of data points based on time elapsed since a start of the video;
- calculate one or more metrics based on the eye tracking data, the one or more metrics comprising at least conjugacy metrics of both eyes of the subject;
- determine a logistic regression model based on the at least one or more metrics; and
- use at least the logistic regression model to compare movement of the first eye to the second eye and predict whether the subject has abnormal eye convergence.

9. The system of claim 8, wherein the instructions for tracking the eye movement of the subject comprises instructions configured to tracking movement of said both eyes of the subject.

10. The system of claim 8, wherein the instructions for generating the eye tracking data are configured to:
- analyze the tracked eye movement; and
- compare the tracked eye movement to a normal or mean eye movement.

11. The system of claim 10, wherein the instructions for generating the eye tracking data are further configured to, after the comparing, calculate a standard deviation or p value for the tracked eye movement as compared to the normal or mean eye movement.

12. The system of claim 8, further comprising instructions for predicting whether a brain injury has occurred in the subject based on determining whether the subject has abnormal eye convergence.

13. System of claim 12, wherein the instructions for predicting whether the brain injury has occurred are configured to determine whether a concussion has occurred by performing a receiver operating curve analysis of the logistic regression model to determine a cut off, and wherein the logistic regression model correlates the one or more metrics with the concussion based on the cut off.

14. A non-transitory computer-readable medium having instructions stored thereon for predicting abnormal eye convergence in a human or animal subject, the instructions configured to perform operations comprising:
- receiving, via an eye tracker having a camera, eye movement data pertaining to pupil positions of both eyes of the subject while watching a video, the eye tracking data including a plurality of data points for said both eyes;
- temporally calibrating the eye tracker by independently predicting the pupil positions of said both eyes of the subject for each of the plurality of data points based on time elapsed since a start of the video;
- analyzing the eye movement data of said both eyes of the subject to determine one or more metrics, the one or more metrics comprising at least conjugacy metrics of said both eyes of the subject;
- determining a logistic regression model based on the one or more metrics; and
- using at least the logistic regression model to compare movement of the first eye to the second eye and predict whether the subject has abnormal eye convergence.

15. A computer-readable medium as in claim 14, wherein the instructions are further configured to perform calculating a standard deviation or p value for eye movement of said both eyes of the subject as compared to a normal or mean eye movement, before the determining of the one or more metrics.

16. A computer-readable medium as in claim 14, wherein the instructions for receiving the eye movement data are further configured to perform operations comprising: tracking eye movement of at least one eye of the subject; collecting raw x and y cartesian coordinates of the pupil positions; and normalizing the raw x and y cartesian coordinates.

* * * * *